(12) United States Patent
Mayer et al.

(10) Patent No.: US 10,709,487 B2
(45) Date of Patent: Jul. 14, 2020

(54) METHOD OF FASTENING A TISSUE OR A CORRESPONDING PROSTHETIC ELEMENT IN AN OPENING PROVIDED IN A HUMAN OR ANIMAL BONE AND FASTENER SUITABLE FOR THE METHOD

(75) Inventors: Jörg Mayer, Niederlenz (CH); Milica Berra, Schlieren (CH); Andrea Mueller, Winterthur (CH); Stephanie Goebel-Mehl, Mettmenstetten (CH); Andreas Wenger, Muri b. Bern (CH); Elmar Mock, Colombier (CH)

(73) Assignee: SPORTWELDING GMBH, Schlieren (CH)

( * ) Notice: Subject to any disclaimer, the term of this patent is extended or adjusted under 35 U.S.C. 154(b) by 1171 days.

(21) Appl. No.: 13/522,611

(22) PCT Filed: Jan. 19, 2011

(86) PCT No.: PCT/CH2011/000005
§ 371 (c)(1),
(2), (4) Date: Sep. 20, 2012

(87) PCT Pub. No.: WO2011/091545
PCT Pub. Date: Aug. 4, 2011

(65) Prior Publication Data
US 2013/0006278 A1    Jan. 3, 2013

Related U.S. Application Data

(60) Provisional application No. 61/298,746, filed on Jan. 27, 2010.

(51) Int. Cl.
*A61B 17/86*    (2006.01)
*A61B 17/68*    (2006.01)
(Continued)

(52) U.S. Cl.
CPC ........ *A61B 17/8645* (2013.01); *A61B 17/686* (2013.01); *A61B 17/864* (2013.01);
(Continued)

(58) Field of Classification Search
CPC ... A61B 17/68; A61B 17/686; A61B 17/7097; A61B 17/7098; A61B 17/84;
(Continued)

(56) References Cited

U.S. PATENT DOCUMENTS

RE34,871 E    3/1995 McGuire et al.
5,906,632 A  *  5/1999 Bolton ............... A61B 17/0401
606/232

(Continued)

FOREIGN PATENT DOCUMENTS

EP    0317406    5/1989
EP    0651979    5/1995
(Continued)

OTHER PUBLICATIONS

Mayr, et al. "Axial Load in Case of Press-Fit Fixation of the ACL Graft—Basic Science", Z Orthop Ihre Grenzgeb, 143 (5): 556-560 (2005), 6 pages.
(Continued)

*Primary Examiner* — Amy R Sipp
(74) *Attorney, Agent, or Firm* — Rankin, Hill & Clark LLP

(57) ABSTRACT

A graft or prosthetic element suitable e.g. for replacing a tendon or ligament is fastened in a bone tunnel or blind opening with the aid of a fastener. In a first step, the graft or prosthetic element is press-fitted in the tunnel or opening by forcing the fastener into the opening or by positioning the fastener in the opening and then expanding it, wherein the fastener is in contact with the graft or prosthetic element and with the bone wall of the tunnel or blind opening. In a
(Continued)

second step, the fastener is anchored in the bone wall of the tunnel or blind opening with the aid of a liquefiable material which is liquefied in the vicinity of the bone wall where it is in contact with the fastener and by making the liquefied material penetrate into the bone wall.

12 Claims, 11 Drawing Sheets

(51) Int. Cl.
    *A61F 2/08*     (2006.01)
    *A61B 17/00*     (2006.01)

(52) U.S. Cl.
    CPC ......... *A61F 2/0811* (2013.01); *A61B 17/8625* (2013.01); *A61B 17/8685* (2013.01); *A61B 2017/00955* (2013.01); *A61F 2/0805* (2013.01); *A61F 2002/0858* (2013.01); *A61F 2002/0882* (2013.01); *A61F 2210/0085* (2013.01)

(58) Field of Classification Search
    CPC ..... A61B 17/844; A61B 17/846; A61B 17/86; A61B 17/8625; A61B 17/864; A61B 17/8645; A61B 17/8841; A61F 2/0811; A61F 2002/0835; A61F 2002/0841; A61F 2002/0858; F16B 13/141; F16B 39/021
    USPC ............................................ 623/13.11–13.12
    See application file for complete search history.

(56) References Cited

U.S. PATENT DOCUMENTS

| | | | |
|---|---|---|---|
| 6,099,530 A * | 8/2000 | Simonian | A61F 2/0811 606/151 |
| 6,379,361 B1 | 4/2002 | Beck | |
| 6,409,730 B1 | 6/2002 | Green et al. | |
| 7,008,226 B2 | 3/2006 | Mayer et al. | |
| 7,335,205 B2 | 2/2008 | Aeschlimann et al. | |
| 7,708,761 B2 | 5/2010 | Petersen | |
| 2001/0007074 A1 | 7/2001 | Strobel | |
| 2002/0013608 A1 | 1/2002 | ElAttrache et al. | |
| 2002/0165611 A1 | 11/2002 | Enzerink et al. | |
| 2004/0030341 A1 * | 2/2004 | Aeschlimann | A61B 17/00491 606/232 |
| 2004/0093031 A1 | 5/2004 | Burkhart et al. | |
| 2006/0105295 A1 | 5/2006 | Mayer et al. | |
| 2007/0038221 A1 * | 2/2007 | Fine | A61F 2/0811 606/323 |
| 2007/0260250 A1 * | 11/2007 | Wisnewski | A61B 17/7098 606/262 |
| 2008/0215091 A1 | 9/2008 | Dreyfuss | |
| 2009/0018590 A1 * | 1/2009 | Dorawa | A61B 17/864 606/301 |
| 2009/0131947 A1 | 5/2009 | Aeschlimann et al. | |
| 2009/0192546 A1 * | 7/2009 | Schmieding | A61B 17/0401 606/232 |
| 2009/0222090 A1 | 9/2009 | Mayr et al. | |
| 2009/0265004 A1 | 10/2009 | Morgan et al. | |
| 2010/0121348 A1 * | 5/2010 | van der Burg | A61B 17/0401 606/139 |
| 2010/0256688 A1 * | 10/2010 | Giersch | A61B 17/68 606/305 |
| 2012/0053691 A1 | 3/2012 | Hays et al. | |
| 2012/0165868 A1 | 6/2012 | Burkhart et al. | |
| 2012/0265299 A1 | 10/2012 | Beck, Jr. et al. | |
| 2012/0283830 A1 | 11/2012 | Myers | |
| 2013/0006302 A1 | 1/2013 | Paulk et al. | |
| 2013/0030479 A1 | 1/2013 | Regauer | |
| 2013/0103100 A1 | 4/2013 | Ruffieux | |
| 2013/0138123 A1 | 5/2013 | Stone et al. | |
| 2013/0144384 A1 | 6/2013 | Gall et al. | |
| 2013/0150885 A1 | 6/2013 | Dreyfuss | |
| 2013/0172998 A1 | 7/2013 | Whittaker | |
| 2013/0184819 A1 | 7/2013 | Donnelly et al. | |

FOREIGN PATENT DOCUMENTS

| | | |
|---|---|---|
| EP | 2486856 | 8/2012 |
| EP | 2596764 | 5/2013 |
| RU | 2 204 963 | 5/2003 |
| WO | 2004017857 | 3/2004 |
| WO | 2006/023661 | 3/2006 |
| WO | 2008/034276 | 3/2008 |
| WO | 2008128588 | 10/2008 |
| WO | 2009/132472 | 11/2009 |
| WO | 2010/045751 | 4/2010 |
| WO | 2010/117982 | 10/2010 |
| WO | 2010/127462 | 11/2010 |

OTHER PUBLICATIONS

Mayr, et al. "Beta-tricalcium Phosphate Plugs for Press-Fit Fixation in ACL Reconstruction—A Mechanical Analysis in Bovine Bone", The Knee, 14 (3): 239-44 (2007), 6 pages.

* cited by examiner

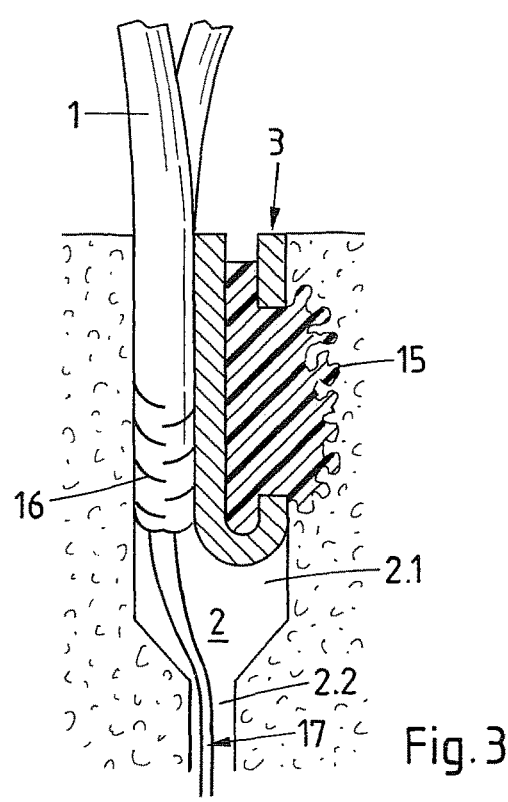
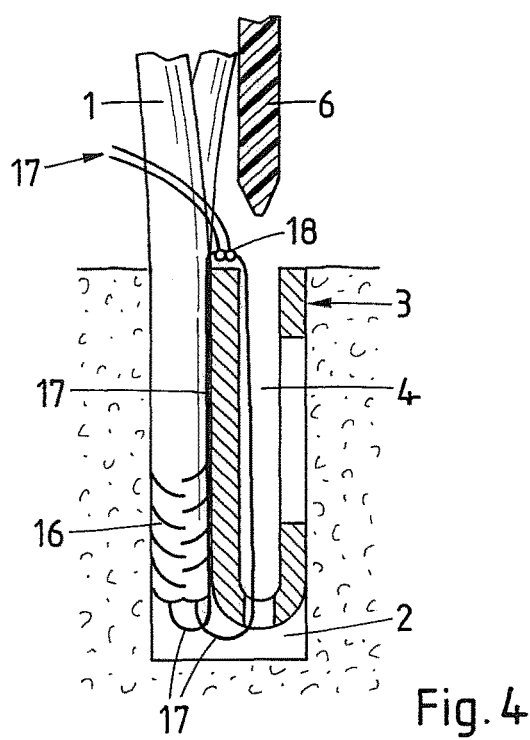
Fig. 3
Fig. 4
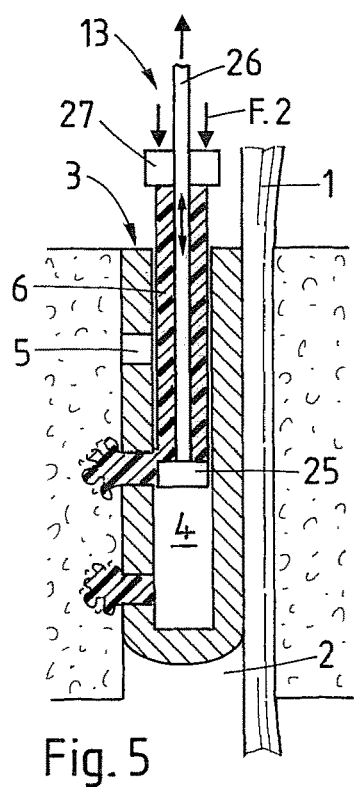
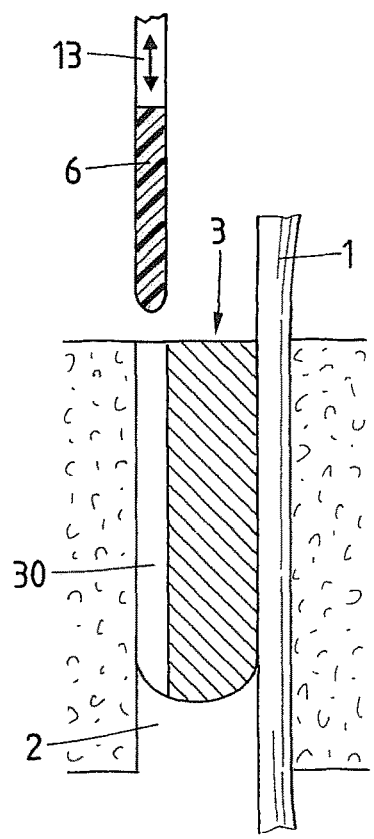
Fig. 5
Fig. 6

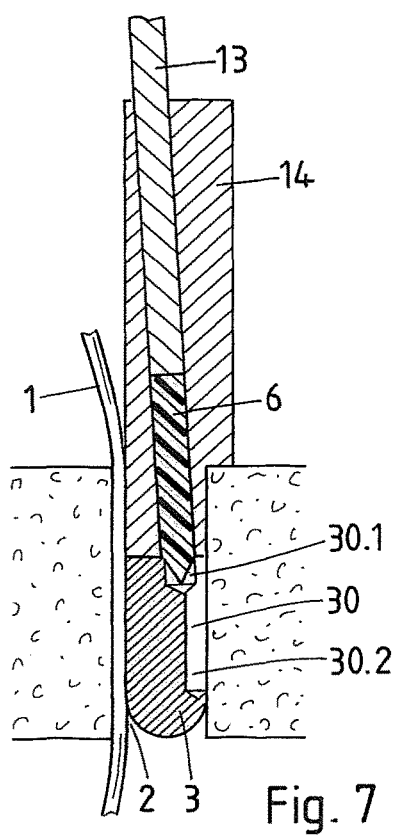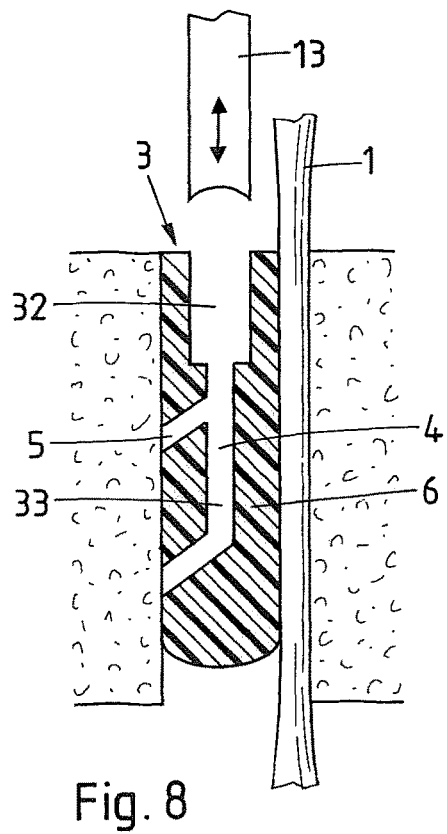
Fig. 7  Fig. 8
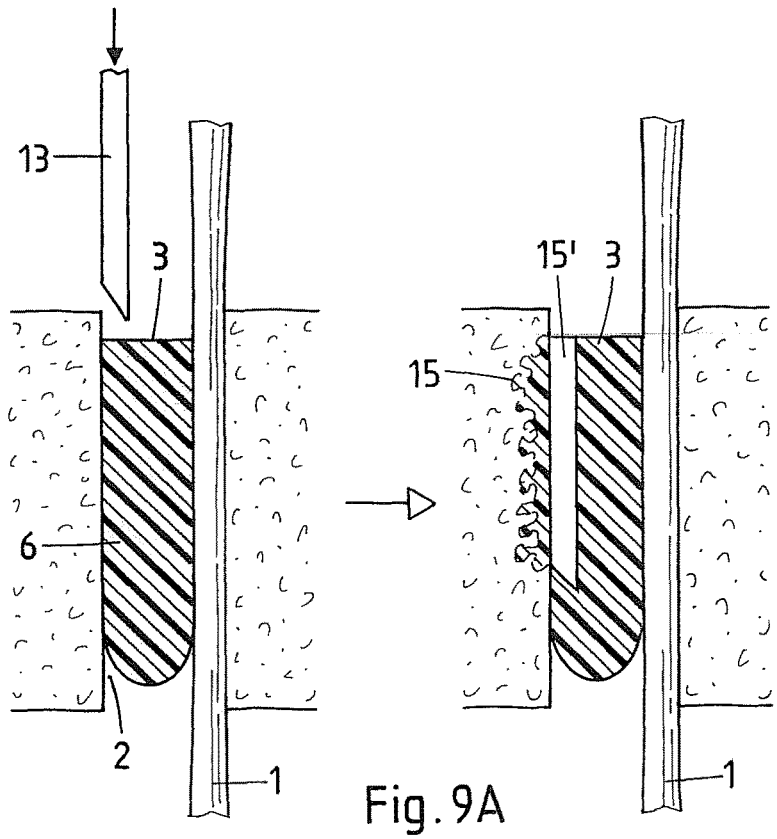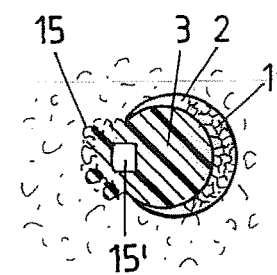
Fig. 9A  Fig. 9B

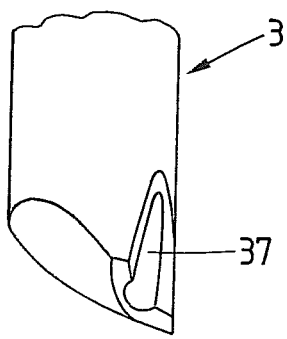
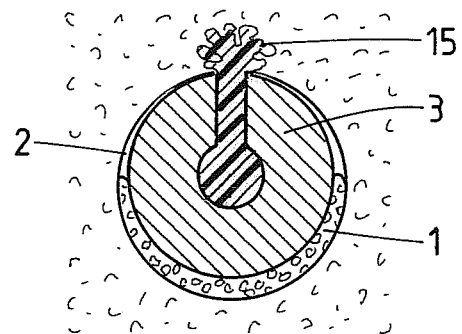
Fig. 17　　　　　Fig. 18
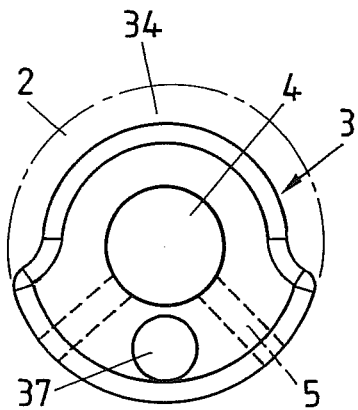
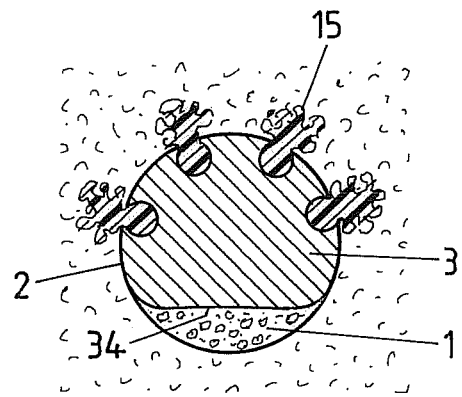
Fig. 19　　　　　Fig. 20
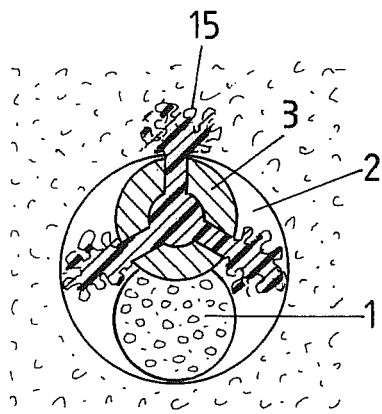
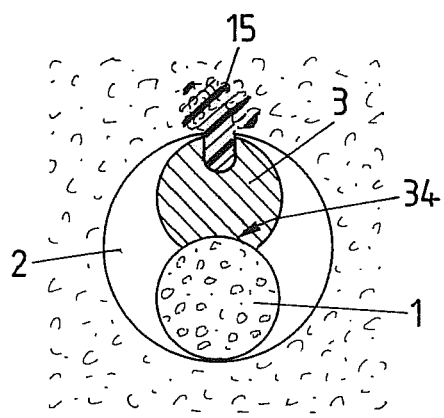
Fig. 21　　　　　Fig. 22

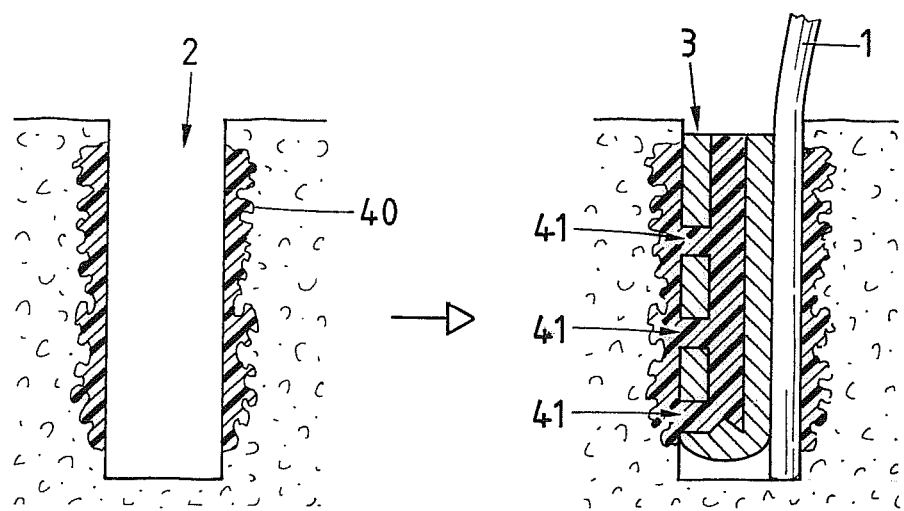
Fig. 23
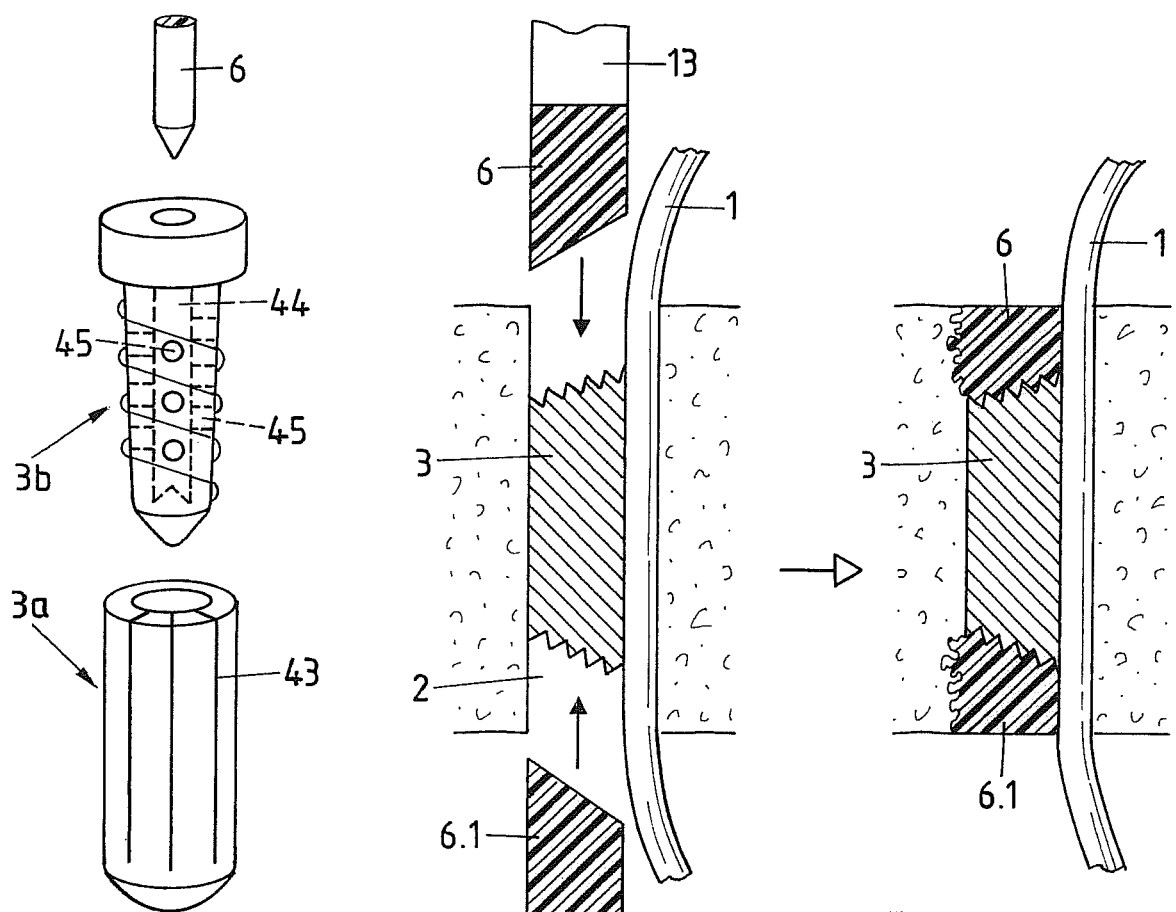
Fig. 24
Fig. 25

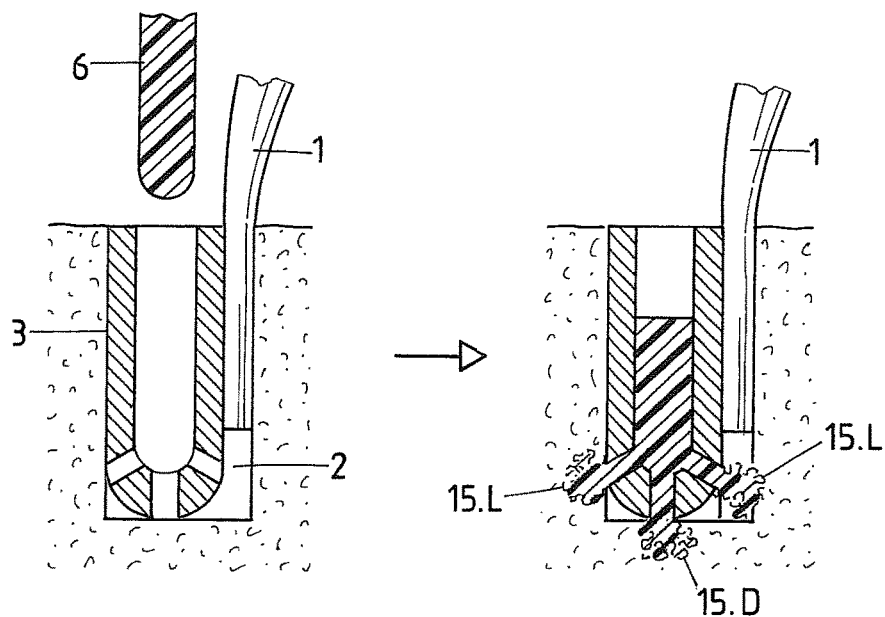
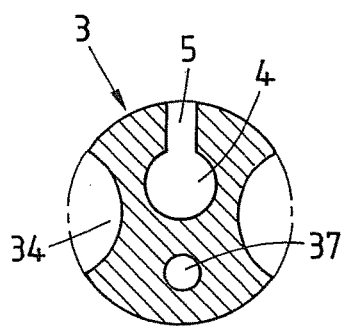 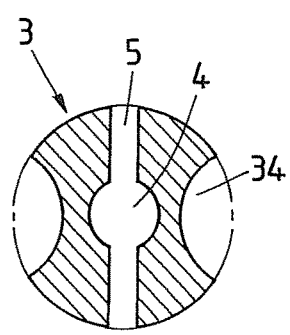 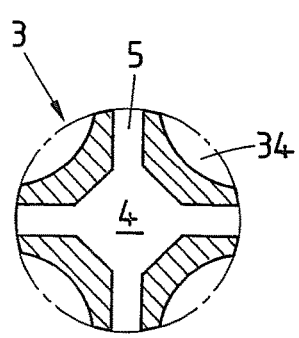
Fig. 27   Fig. 28   Fig. 29
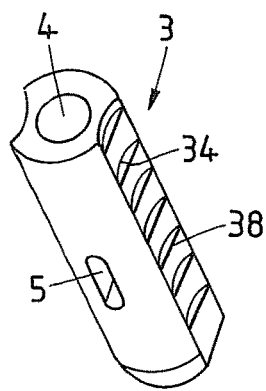 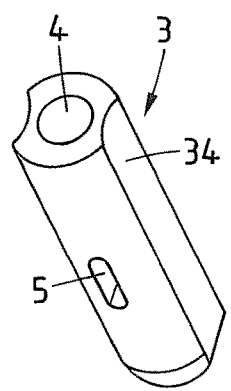 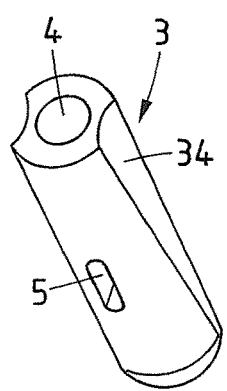 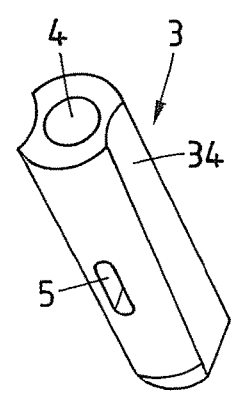
Fig. 30   Fig. 31   Fig. 32   Fig. 33

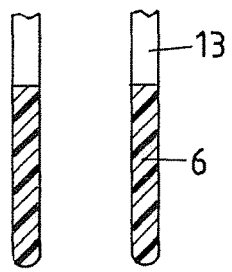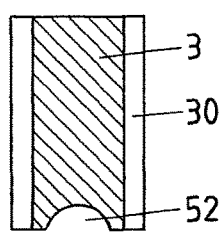
Fig. 34A
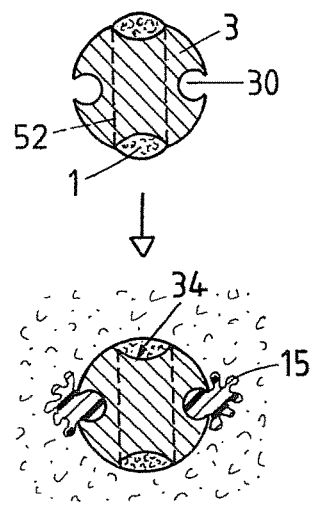
Fig. 34B
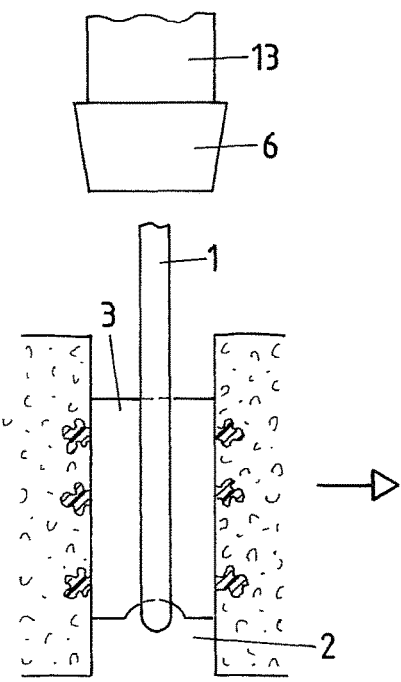
Fig. 35A
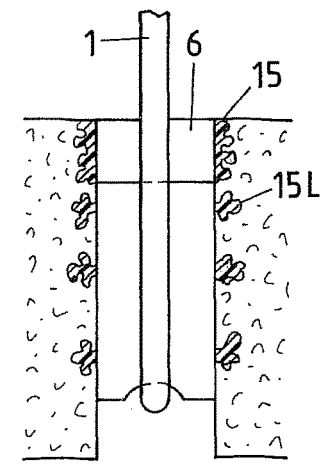
Fig. 36
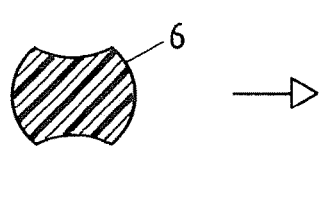
Fig. 35B

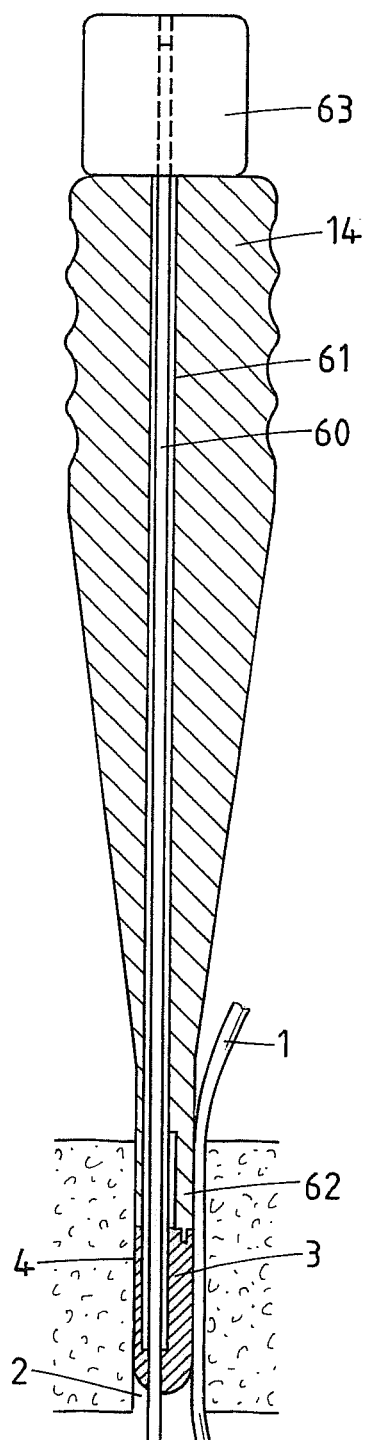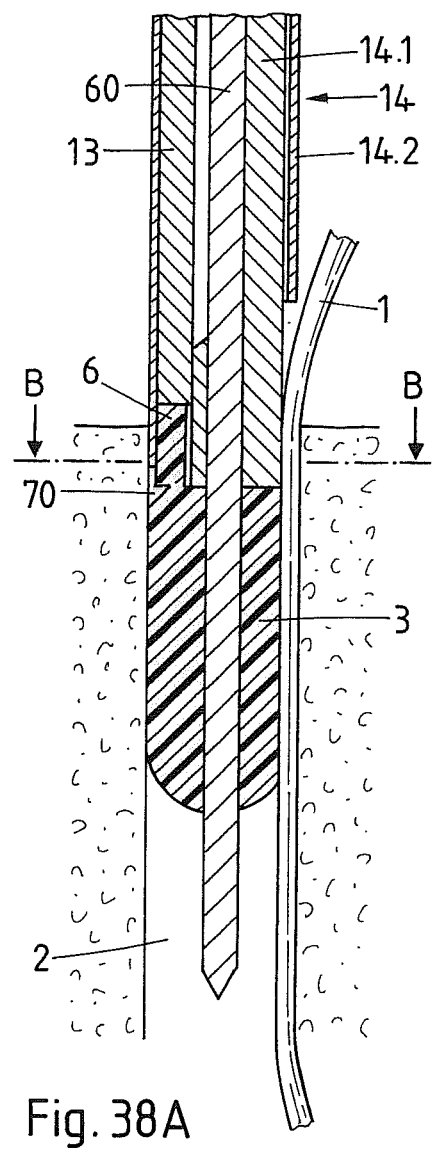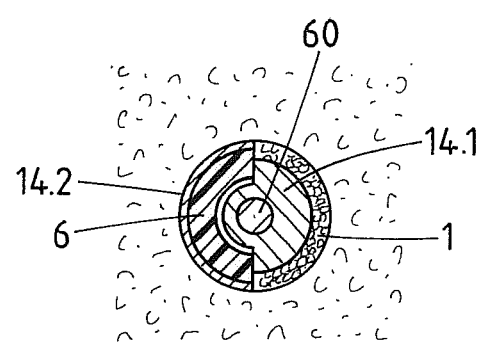
Fig. 37
Fig. 38A
Fig. 38B

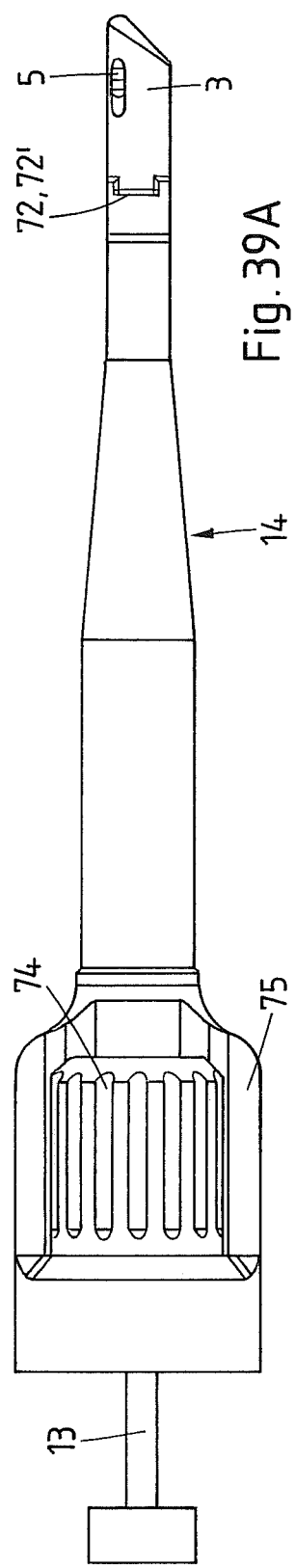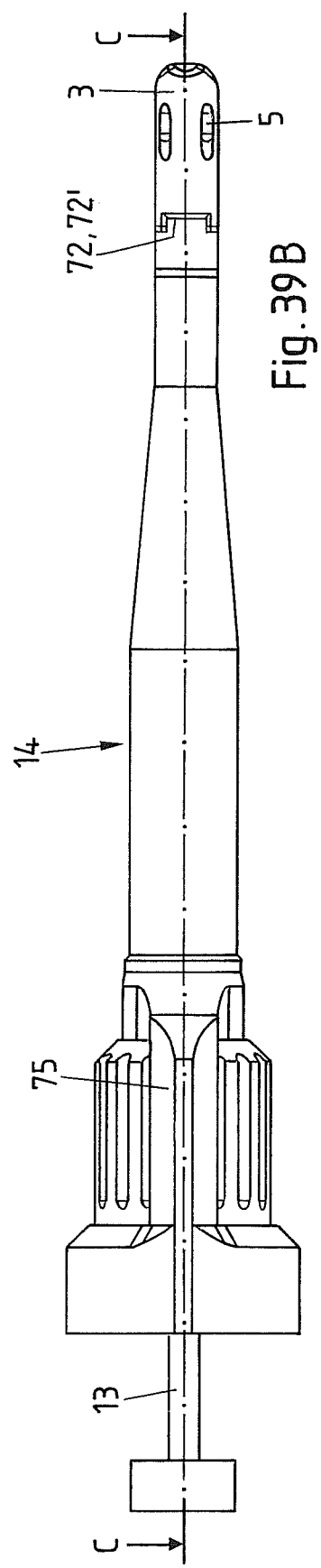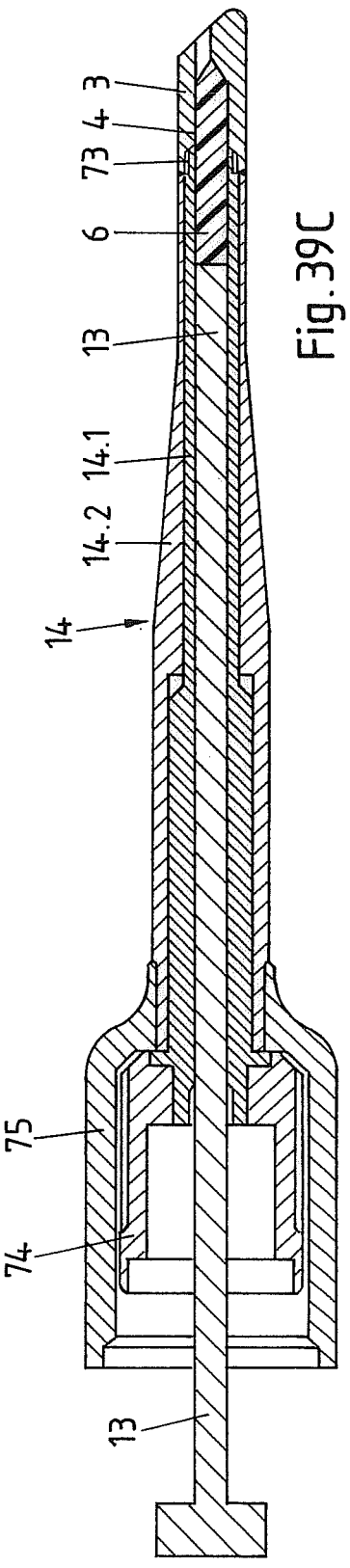

METHOD OF FASTENING A TISSUE OR A CORRESPONDING PROSTHETIC ELEMENT IN AN OPENING PROVIDED IN A HUMAN OR ANIMAL BONE AND FASTENER SUITABLE FOR THE METHOD

FIELD OF THE INVENTION

The invention belongs to the field of orthopedic surgery and concerns a method of fastening a tissue or a corresponding prosthetic element in an opening provided in a human or animal bone. The invention further concerns a fastener being suitable for the method.

The tissue or prosthetic element to be fastened, with the aid of method and fastener according to the invention, in an opening provided in a human or animal bone has the function of a soft tissue and is in particular a ligament or tendon graft (e.g. bone-tendon-bone graft or tendon graft with at least one stitched end) or an artificial ligament or tendon substitute or partial substitute for replacing or strengthening a ruptured or otherwise defect ligament or tendon, but this tissue may also be a natural ligament or tendon to be re-attached to a bone from which it has been detached by injury or surgery. This means that the tissue or corresponding prosthetic element is in particular a soft tissue, a soft tissue graft or a soft tissue substitute or partial substitute, which may however, where it is to be fastened to the bone, comprise a piece of bone tissue or of a corresponding replacement material, which is attached to the soft tissue and which in this case is fastened in the opening. One or both ends of the tissue or corresponding prosthetic element to be fastened may be strengthened or in particular in the case of a graft comprising a plurality of strands may be held together by stitching, wherein suture ends extending away from the graft may also used for positioning and tensioning the graft.

The opening provided in the bone for the fastening is in a per se known manner a tunnel leading through the bone or a blind opening extending into the bone from a bone surface and comprising within the bone a closed end. This opening is preferably provided by drilling but can also be provided by e.g. punching (e.g. ultrasonic punching), i.e. this opening will often have a circular or non-circular cross section remaining constant over most of the depth of the opening, but this is not a condition for the invention. The opening may also have a plurality of sections with differing cross sections, may have a conical form, or may be undercut. (e.g. made by milling which allows to produce three dimensional geometries within the opening).

One exemplary application of the method and fastener according to the invention is the replacement of a ruptured anterior cruciate ligament (ACL) in a human knee by a graft which is fastened on the one hand in an opening extending from the tibia plateau and on the other hand in an opening extending from the articular surface of the distal femur end.

BACKGROUND OF THE INVENTION

According to the state of the art, a ruptured anterior cruciate ligament is replaced e.g. by a graft, such as e.g. a patellar tendon graft comprising two terminal bone blocks, a hamstring tendon graft (semitendinosus tendon, possibly combined with gracilis tendon), usually being folded and stitched in the end region, i.e. not comprising terminal bone blocks, or a quadriceps tendon graft, which is usually harvested with one terminal bone block. The named grafts are usually autografts but may also be donor grafts (allografts). Donor grafts may also be made of achilles tendons. It is further proposed to use synthetic ribbons (herein called "artificial grafts") and suitably treated tendon material of slaughtered animals (xenografts), e.g. pigs. The named autografts and allografts may furthermore be reinforced with synthetic material and be combined with bone grafts or synthetic bone substitutes End regions of all the named grafts (autografts, allografts, xenografts and artificial grafts) need to be fastened in tibia and femur for which purpose a tunnel or a blind bore is provided in either one of the two bones. The blind bore originates from the articular surface and ends inside the bone. The tunnel has a first mouth situated in the articular surface and a second mouth which is not situated in the articular surface, wherein the first mouth and adjoining tunnel portion may have a larger cross section than the second mouth and adjoining tunnel portion. For fastening the graft in the provided opening a plurality of fastener types is known.

A tunnel allows fastening at the inner bone wall of the tunnel (inner fixation) and/or in the vicinity of the second tunnel mouth (outer fixation), a blind opening allows inner fixation only. According to the state of the art inner fixation in a bone opening is effected e.g. with the aid of an interference screw, which is screwed into the opening when the graft is positioned therein; with the aid of a non-threaded, mechanically expandable or non-expandable press-fit element, which is forced without rotation into the opening when the graft is positioned therein or together with the graft; or with the aid of a cross pin which is implanted at an angle to the axis of the opening and engages e.g. a folded end of the graft or a suture loop attached to the graft end. In blind openings inner fixation can also be effected with the aid of a bone screw comprising a head section to which the graft is fixed (hook screw) and which is screwed into the bottom of the blind opening. Inner fixation in a tunnel is usually completed by closing the second tunnel mouth with a bone plug or similar prosthetic element. Various devices and methods for inner fixation are described e.g. in the publications U.S. Pat. Nos. 5,454,811 and 6,099,530 (both to Smith & Nephew), EP-0317406 (Laboureau), or US-2009/222090 (Mayr).

Outer fixation (fixation in the area of a second tunnel mouth not situated in the articular surface) according to the state of the art is effected e.g. with the aid of a button through which the folded graft or a suture loop attached to a graft end is threaded and which is larger than the cross section of the second mouth, or with the aid of a bone screw or similar anchor element which holds the graft or suture ends attached thereto and is screwed or impacted into the bone in the vicinity of the second tunnel mouth. Such outer fixation is also proposed for reinforcing an inner fixation inside the tunnel.

For an inner fixation in a bone tunnel or blind opening with the aid of a fastener such as an interference screw or a press-fit element, the graft or an end portion of the graft respectively is pressed against one side of the opening, while the fastener occupies the other side of the opening. This so called extra-graft fixation is mainly used for one-strand grafts and for grafts comprising a terminal bone block but may also be used for multi-strand grafts. For grafts comprising two strands by e.g. being folded over, the fastener may also be positioned between the two strands separating them from each other, wherein the separated strands are pressed against opposite walls of the bone opening. Such fixation is called intra-graft fixation. Intra-graft fixation is also used for grafts of four or more than four strands, wherein the strands of the graft are pressed against the wall of the bone opening, preferably substantially regularly spaced around the fastener and wherein, between neighboring strands the fastener may or may not be in contact with the bone wall of the opening. Intra-graft fixation is proposed in particular for the graft end at which the strand or strands are folded.

The publication WO 2006/023661 (Scandious Biomedical) discloses a large number of known methods of ACL-fixation, in particular intra-graft fixation with the aid of press-fit fasteners which are additionally secured in the bone tunnel or blind bore.

The quality of most inner graft fixations is in particular dependent on the interface between the graft and the fastener on the one hand and between the graft and the wall of the opening on the other hand, but in most cases it is also dependent on the interface between the fastener and the wall of the opening, wherein good primary stability is desired at all the named interfaces and good long-term stability in particular at the interface between graft and bone tissue (good integration of the graft in the natural tissue by natural tissue growth after the fixation operation). The fixation quality is found to be further depending on the fixation location in the opening, wherein fixation as close to the articular surface seems to be advantageous. For shortening convalescence, good primary stability is desired, for good long-term stability, bone growth in the opening. For allowing a maximum of bone growth in the opening, bioresorbable interference screws and press-fit elements are proposed. Furthermore, it is important that the fastener causes as little damage as possible to the graft neither when being implanted nor later on, and that the graft causes as little widening or other damage as possible to the mouth of the opening, in particular for the case in which this mouth is situated in an articular surface.

The most common failures of known soft tissue fixation methods are caused by graft or tissue damage through the threads of interference screws which can lead to graft or tissue rupture, graft or tissue slippage due to relaxation of a corresponding press fit, or fastener migration on first loading e.g. due to compression of bone tissue in response to anchoring elements such as e.g. barbs, which may lead to loss of tension in the graft or soft tissue.

Known fixation of ligaments other than the anterior cruciate ligament (graft or prosthetic element, or re-attachment of natural ligament), of tendons (graft or prosthetic element, or re-attachment of natural tendon), or of other mainly soft tissues (graft or prosthetic element, or repair) in a bone opening provided for the fixation, with the aid of a fastener are based on the same principles as the above shortly described known fixations used for fastening ACL-grafts in openings provided in tibia and femur. Such fixations are e.g. used in surgical procedures regarding the human foot or ankle, such as e.g. lateral ankle reconstruction, FDL tendon transfer (flexor digitorum longus), FHL tendon transfer (flexor hallucius longus), or flexor to tendon transfer (second toe); surgical procedures regarding the human hand such as e.g. ligament reconstruction tendon interposition, scapholunate ligament reconstruction, collateral ligament reconstruction, or UCL repair (ulnar collateral ligament) of the thumb (also known as "gamekeeper's thumb"); surgical procedures regarding the human elbow such as e.g. UCL repair (ulnar collateral ligament), or distal biceps tendon repair; or surgical procedures regarding the human shoulder such as e.g. proximal biceps tendon repair. A further example is the repair of torn or damaged cranial cruciate ligaments (CCL) in stifle joints of dogs in particular but also of e.g. cats. The CCL is the most commonly damaged stifle ligament in dogs and the named repair is e.g. carried out using nylon bands which are passed around the fabella bone in the back of the femur and are fixed in a bore provided in the front part of the tibia. The same as known fixation methods, the fixation according to the invention is suitable for all the named applications.

SUMMARY OF THE INVENTION

The object of the invention is to create a further method and fastener for fastening tissue or a corresponding artificial element (to be understood as: fastening of autograft, allograft, xenograft, or corresponding prosthetic element substituting natural tissue, or repair of natural tissue fixation) inside an opening ("inner fixation" inside a tunnel or inside a blind opening) provided in a human or animal bone, wherein method and fastener according to the invention are to be simple and suitable for a large number of different types of tissues and prosthetic elements as well as for a large number of different types of applications and operation techniques (in particular arthroscopic type surgery) without the necessity of substantial adaptation. In particular, method and fasteners according to the invention are to be suitable without substantial adaptation to be used in anterior cruciate ligament replacement surgery using any type of graft (one-strand, two-strand or multi-strand autograft, allograft, xenograft, or artificial graft, with or without terminal bone block or corresponding artificial graft part and with or without stitched end portions).

The named objects are achieved by method and fastener as defined in the appended claims.

The fixation produced with method and fastener according to the invention is an "inner" fixation (fastener is positioned in the tunnel or blind opening and fastens the tissue to the inside wall of the opening) and is basically a combination of press-fitting the graft in the opening using a fastener which clamps the graft against a first portion of the wall of the opening and subsequent anchoring of the fastener in a second portion of the wall of the opening by establishing a positive-fit connection between the anchor and this second wall portion. This means that the press-fit and the positive-fit are effected after each other, locally separated from each other and fully independent of each other.

The press-fit connection is achieved in a per se known manner using a fastener dimensioned for being forced into the opening (corresponding dimensioning of fastener and opening) or using a fastener which is positioned in the opening and is then expanded, wherein forcing or positioning the fastener in the opening is carried out either when the tissue or artificial element to be fastened is already positioned in the opening or together therewith and wherein forcing or positioning without rotation of the fastener is preferred but not a necessity. The tissue or artificial element to be fastened is arranged in the opening such that it does not cover the whole wall of the opening and the fastener is oriented such that a fastener portion equipped for achieving the positive-fit connection is facing a wall portion not covered by the tissue.

The positive-fit connection is achieved with the aid of an anchoring element comprising a material capable of being liquefied by application of energy (preferably a material having thermoplastic properties), by liquefying the material in situ such that the liquefied material is capable to penetrate preferably the trabecular structure of the bone tissue of the wall of the opening, where on re-solidification it constitutes an anchorage in the form of a positive-fit connection. The anchoring element is positioned relative to the fastener before or after press-fitting the fastener in the opening and is then advanced relative to the fastener using an anchoring tool which simultaneously transmits the energy needed for the liquefaction to the anchoring element or to the fastener. For preventing possible weakening of the press-fit established before the anchoring process, the force used for advancing the anchoring element needs to be small compared with the force used for establishing the press-fit and/or needs to be counteracted such that it does not urge the fastener in a direction in which it was forced into the opening.

It is possible also to firstly treat the bone wall of the opening with a first portion of liquefiable material such that the trabecular structure of this wall is penetrated and therewith re-enforced by the liquefiable material and only then press-fitting fastener and graft in the opening and carrying out the above described anchoring step, wherein a second portion of liquefiable material is welded to the pretreated wall of the opening. This two step anchoring procedure results in a same positive-fit connection as the above described single step procedure if the first and second portions of liquefiable material comprise the same liquefiable material. However, the first and second portions may comprise different liquefiable materials under the condition that the two materials are weldable to each other under the conditions of the anchoring step. For achieving a good anchorage it may be advantageous or even necessary to provide, in addition to or in place of pores or cavities of the trabecular network of the bone tissue, further cavities in the bone wall of the opening to be filled with the liquefied material (e.g. undercut form of opening in the bone tissue).

For the separate fastener functions of pressing (press-fit connection with tissue to be fastened) and anchoring (positive-fit connection with bone tissue of the wall of the opening), the fastener according to the invention comprises separate surface portions equipped either for the pressing function or for the anchoring function. The surface portions equipped for the pressing function may, in a per se known manner, have a flat or concave form (shallow groove) and be rough or otherwise structured for retention of the tissue to be fastened, but may also lack any specific form or structure. The surface portions equipped for the anchoring function comprise means for guiding liquefiable material comprised by the anchoring element from the fastener inside or the proximal fastener face to these surfaces portions and they may further comprise reaming or cutting edges, threads, barbs or other per se known structures for additional support of the fastener in the bone wall of the opening.

In a preferred fastener embodiment the surface portions equipped for either pressing or anchoring constitute sectors of a circumferential surface, wherein a fastener suitable for extra-graft fixation comprises one pressing sector and one anchoring sector and a fastener suitable for intra-graft fixation comprises a plurality of such sector pairs. Alternatively, the fastener surface portions equipped for either pressing or anchoring may be arranged beside each other along a fastener axis, or such alternatively arranged surface portions may be provided on the fastener in addition to the above named surface sectors.

The fastener according to the invention has e.g. the general form of a cylinder, frustum or cone (continually tapering or stepped), preferably but not necessarily with substantially circular cross sections, i.e. is suitable for being fitted into an opening of a substantially circular cross section (cylindrical or tapering continually or in steps), but it may also have another form such as e.g. a parallelepiped or wedge. A fastener according to the invention having the form of a substantially circular cylinder, frustum or cone may comprise in addition to the above named means for guiding the liquefiable material and possibly the means for accommodating the graft, a thread extending around the whole fastener circumference or around only part thereof.

The method according to the invention comprises basically four steps:
(a) providing a fastener and at least one anchoring element comprising a liquefiable material and providing an opening in a bone (e.g. by antegrade or retrograde drilling or by punching), wherein fastener and opening are adapted to each other and to the graft (understood to include natural tissue and a corresponding artificial element) to be fastened,
(b) press-fitting the graft in the opening, wherein the graft is not to cover all of the inner wall of the opening, the press-fitting being carried out by forcing (or positioning and expanding) the fastener into the opening after positioning the graft or together with the graft, and
(c) anchoring the fastener in the bone tissue of the wall of the opening by positioning the at least one anchoring element relative to the fastener and by transferring energy to the liquefiable material comprised by the anchoring element and simultaneously advancing the anchoring element relative to the fastener and therewith liquefying at least part of the anchoring element and making it to penetrate into the wall of the opening (or to be welded to the pretreated wall of the opening), where this wall is not covered by the graft, and
(d) letting the liquefied material re-solidify in the wall of the opening.

The main advantages of the fixation according to the invention is an improvement of the primary stability of the fixation as compared with known press-fit fasteners as e.g. described by H. O. Mayr et. al. in "Axial load in case of press-fit fixation of ACL graft—a fundamental study" (Z Orthop Ihre Grenzgeb, 143(5): 556-60 (2005)) and "Beta-tricalcium plugs for press-fit fixation in ACL reconstruction—a mechanical analysis in bovine bone" (Knee 14(3): 239-44 (2007)). Compared with the known fixation using an interference screw, the fixation according to the invention is possible with substantially reduced danger of mechanically damaging the graft to be fastened and is substantially less dependent on the mechanical properties of the bone tissue in which the opening is provided (allowing fixation in e.g. bone tissue weakened by osteoporosis), because the liquefiable material is additionally able to strengthen this bone tissue. Further compared with the interference screw fixation, the fixation according to the invention preferably uses a fastener without thread and therefore of a smaller diameter, which allows a plurality of fasteners to be implanted closer together. This means that e.g. an ACL graft can be fixed in more than one opening resulting in a fixation of a wider footprint and therefore closer resembling the natural ACL-fixation.

Furthermore, the fixation according to the invention can be carried out without putting a critical thermal load on the graft to be fastened and is therefore suitable for such graft which is not only mechanically sensitive but also thermally.

As mentioned already further above, the anchoring technique applied in the method according to the invention is based on in situ liquefaction of a liquefiable material, in particular of a material having thermoplastic properties. Such anchoring techniques and fastening devices being suitable for such anchoring techniques are disclosed e.g. in the publications U.S. Pat. Nos. 7,335,205, 7,008,226, US 2006/0105295, US-2009/131947, WO-2009/132472, WO-2008/034276, WO-2010/127462, and WO-2010/045751, as well as in the US provisional application US-61/259,383, which is not published yet. The entire disclosure of all the named publications and applications is enclosed herein by reference.

The main features of the named implantation techniques is the in situ liquefaction of a liquefiable material, penetration of the liquefied material into a hard tissue surface (trabecular structure and/or suitable structures or cavities provided in the hard tissue surface) and re-solidification of the liquefiable material in the hard tissue surface. Therein, the liquefiable material is preferably a material having thermoplastic properties, and being able, in its solid state, to transmit energy and, in its liquefied state, to penetrate a trabecular or similar porous structure. Suitable liquefaction connected with an acceptable thermal loading of the tissue is achievable by using materials with thermoplastic properties preferably having a modulus of elasticity of at least 0.5 GPa and a melting temperature of up to about 350° C. and by liquefying only a necessary minimum amount of the material. The energy applied for such liquefaction is preferably mechanical vibration energy of a frequency preferably in the range of between 2 and 200 kHz (preferably ultrasonic vibration with a frequency preferably between 15 and 30 kHz, even more preferably between 20 and 25 kHz), wherein the liquefiable material and possibly other portions of the fastener or anchoring element transmit the vibration, preferably with very little damping to localities where the liquefiable material e.g. vibrates against a counter element thereby causing friction and therewith liquefaction.

Instead of using vibrational energy for creating the local thermal energy needed for the liquefaction of the material with thermoplastic properties, it is possible also to exploit other energy types, in particular rotational energy turned into friction heat in substantially the same manner as the vibrational energy, or electromagnetic radiation (in particular laser light in the visible or infrared frequency range), which radiation is preferably guided through the material with thermoplastic properties and locally absorbed by an absorber being contained in the material with thermoplastic properties or being arranged adjacent to this material. Electric energy can also be used.

Suitable liquefiable materials for the anchoring element used in the fixation method according to the invention are thermoplastic polymers, e.g.: resorbable polymers such as polymers based on lactic and/or glycolic acid (PLA, PLLA, PGA, PLGA etc.) or polyhydroxy alkanoates (PHA), poly-caprolactone (PCL), polysaccharides, polydioxanes (PD) polyanhydrides, polypeptides or corresponding copolymers or composite materials containing the named polymers as a component; or non-resorbable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers (LCPs), polyacetales, halogenated polymers, in particular halogenated polyolefines, polyphenylensulfides, polysulfones, polyethers or equivalent copolymers or composite materials containing the named polymers as a component.

Specific embodiments of degradable materials are Polylactides like LR706 PLDLLA 70/30, 8208 PLDLA 50/50, L210S, and PLLA 100% L, all by Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in CA Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, Polycarbonateurethane (in particular Bionate by DSM, in particular type 65D and 75D). An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec).

The liquefiable material having thermoplastic properties may contain foreign phases or compounds serving further functions. In particular, the thermoplastic material may be strengthened by admixed fibers or whiskers (e.g. of calcium phosphate ceramics or glasses) and such represent a composite material. The thermoplastic material may further contain components which expand or dissolve (create pores) in situ (e.g. polyesters, polysaccharides, hydrogels, sodium phosphates), compounds which render the fusion device opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed. If the device is to be anchored not with the aid of vibration energy but with the aid of electromagnetic radiation, the liquefiable material having thermoplastic properties may locally contain compounds (particulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tri-calciumphosphate (TCP), Hydroxyapatite (HA, <90% crystallinity; or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% crystallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), JA Juhasz et al. Biomaterials, 2004 March; 25(6):949-55. Particulate filler types include: coarse type: 5-20 μm (contents, preferentially 10-25% by volume), sub-micron (nanofillers as from precipitation, preferentially plate like aspect ratio>10, 10-50 nm, contents 0.5 to 5% by volume). Experiments show that liquefaction with the aid of ultrasonic vibration energy allows filling the thermoplastic polymer to a relatively high degree without impairing the capability of the liquefied material to penetrate structures as e.g. the trabecular structure of viable cancellous bone.

BRIEF DESCRIPTION OF THE DRAWINGS

Exemplary embodiments of the method and the fastener according to the invention are described in detail in connection with the appended Figs., wherein:

FIGS. 3 and 4 illustrate two further exemplary applications of graft fixation according to the invention, in a bone tunnel comprising a portion of a reduced diameter (FIG. 3) or in a blind bore (FIG. 4);

FIGS. 5 to 9A/B show further exemplary sets comprising a fastener, anchoring element and an anchoring tool, the sets being suitable for the fixation method according to the invention;

FIGS. 10 to 17 are three-dimensional illustrations or axial sections of further exemplary fastener embodiments which are suitable for methods similar to the ones illustrated in FIGS. 1 and 5;

FIGS. 18 to 22 are cross sections through grafts being fixated with the method according to FIG. 1, 5, 6 or 7 in a bone tunnel or blind bore with the aid of further exemplary fastener embodiments;

FIG. 23 shows an embodiment of the method according to the invention including a pretreatment step in which the wall of the opening is treated with a first portion of liquefiable material before introduction of the fastener;

FIG. 24 shows an embodiment of the method according to the invention, wherein an expandable fastener is used;

FIG. 25 illustrates a further exemplary embodiment of the method according to the invention, the method being suitable for an extra-graft fixation in a bone tunnel or in a blind opening;

FIG. 26 shows a further exemplary embodiment of the method according to the invention, the method being suitable for an extra-graft fixation in a blind opening;

FIGS. 27 to 33 are cross sections and three dimensional representations of exemplary fastener embodiments suitable for intra-graft fixation using a method similar to the one as illustrated in FIG. 1 or 5;

FIGS. 34A/B show an exemplary embodiment of a set according to the invention, the set comprising fastener, anchoring element and anchoring tool and being suitable for an intra-graft fixation using a method similar to the one as illustrated in FIG. 6 or 7;

FIGS. 35A/B show an exemplary embodiment of a set according to the invention, the set comprising fastener, anchoring element and anchoring tool and being suitable for an intra-graft fixation using a method similar to the one as illustrated in FIG. 25;

FIG. 36 shows an exemplary footprint of a fixation of a two strand graft according to the invention, which footprint is in particular suitable for the tibial ACL fixation;

FIGS. 37, 38A/B and 39A/B/C show sets of fastener, anchoring element, anchoring tool, and guide tool, wherein the guide tool is suitable not only for guiding the anchoring tool during the anchoring process, but also for forcing the fastener into the opening along a guide wire for establishing the press fit before the anchoring process is started.

Items having the same function and similar items are denominated in all Figs. with the same reference numerals.

DESCRIPTION OF PREFERRED EMBODIMENTS

Figure 1:
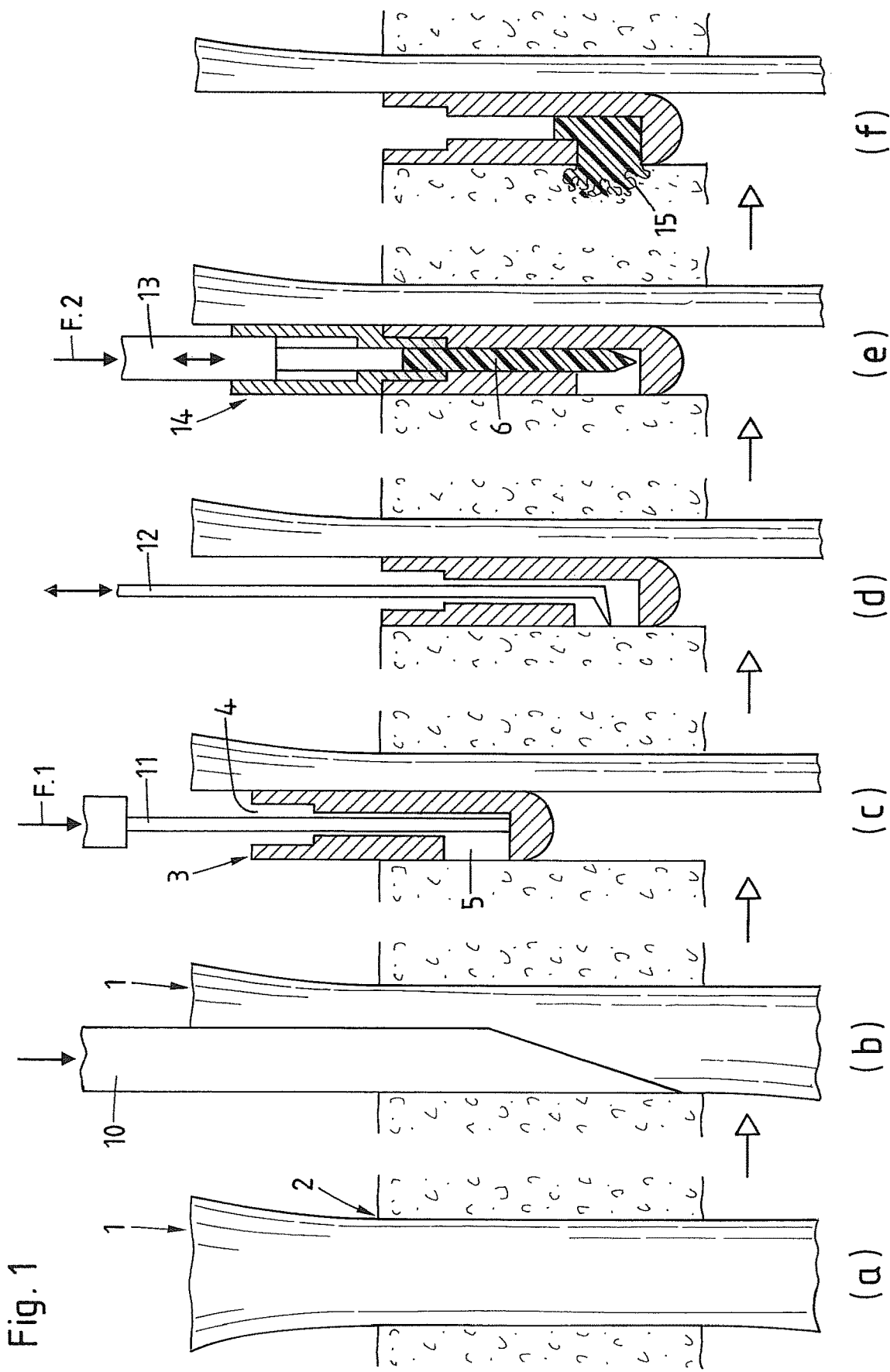
FIG. 1 illustrates the invention by showing six consecutive phases of an exemplary extra-graft fixation in a bone tunnel using an exemplary embodiment of the method according to the invention.

FIG. 1 shows six consecutive phases (a) to (f) of the fixation (extra-graft fixation) of a soft tissue in a bone tunnel using exemplary embodiments of method and fastener according to the invention. The soft tissue is e.g. a graft 1, which, as seen from phase (a), is positioned to extend through the tunnel 2 and, if applicable, is kept with per se known measures at a desired tension during the fixation process. However, neither the method nor the fastener need to be different for fastening a prosthetic element or a natural soft tissue in the tunnel, wherein the graft or soft tissue may not extend through the tunnel but have an end inside the tunnel, and at this end may comprise a terminal bone block. Obviously in the latter case the opening may also be a blind opening, e.g. a blind bore. Furthermore, the graft or soft tissue may comprise a stitched end portion with suture ends extending therefrom, wherein this end portion is positioned in the tunnel, the suture end portions exiting through the second tunnel mouth and being used e.g. for tensioning the graft or soft tissue (see also FIG. 3).

The fastener 3 is adapted in cross section for being capable of press-fitting the graft 1 in the tunnel 2. The fastener 3 comprises an inner cavity 4, which is e.g. substantially cylindrical, which extends from the proximal fastener face towards the distal fastener end, and which is connected by a passage 5 or a plurality of passages to an anchoring sector of the circumferential fastener surface, i.e. to one only side of the fastener 3. The passage 5 may have the form of one or a plurality of e.g. slot-shaped, round or polygonal fenestrations or of an otherwise perforated region (e.g. material with an open porosity, e.g. trabecular or sintered metal or ceramic). The anchoring element 6 is e.g. a pin-shaped item of a material having thermoplastic properties which material is suitable to be liquefied in the above described manner, the anchoring element fitting into the inner cavity 4 to reach at least into the region of the passage 5.

The fixation process is preferably carried out as follows: The graft 1 positioned through the tunnel 2 as shown in phase (a) is impacted against one side of the tunnel wall by introducing a dilator 10 between the graft 1 and the opposite side of the tunnel wall as shown in phase (b), wherein a one-sided tapering dilator 10 as illustrated and used with the tapering side facing the graft 1 proves the most effective. This impaction compresses the graft 1 or, if applicable, the terminal bone block thereof. In phase (c) the dilator 10 is removed and the fastener 3 is forced (force F.1) into the space between the graft 1 and the tunnel wall which space has been prepared in the impaction step. Therein the passage 5 of the fastener 3 faces towards the tunnel wall opposite the graft 1 and the positioned fastener 3 is to press-fit the graft against the tunnel wall. For forcing the fastener 5 into the tunnel, e.g. a push rod 11 reaching into the inner fastener cavity 4 is used. Instead of using the illustrated push rod 11 for forcing the fastener into the tunnel, a ram tool acting on the proximal fastener face may also be used. In phase (d) the push rod 11 is removed and a reamer 12 is introduced into the inner fastener cavity 4, its angled distal tip directed to reach through the passage 5. The reamer 12 is reciprocated for reaming the tunnel wall outside the passage 5. In phase (e) the reamer 12 is removed and the anchoring element 6 is introduced in the inner cavity 4 and an anchoring tool 13 is placed on the proximal face of the anchoring element 6 or fixed thereto. Therein it is advantageous to also position a guide tool 14, this guide tool being equipped for guiding the anchoring tool 13 and possibly the anchoring element 6 for being able to be advanced exactly coaxially in the inner cavity 4. The anchoring tool 13 serves for producing the anchorage of the fastener through the anchoring element in the tunnel wall, i.e. for transmitting to the anchoring element 6 energy, e.g. ultrasonic vibration, needed for liquefaction of the liquefiable material and a force F.2 for advancing the anchoring element 6 towards the distal fastener end, such that the material of the anchoring element 6 is liquefied and, in a liquid state is made to flow through the passage 5 into the bone tissue of the tunnel wall, where on re-solidification it constitutes an anchorage 15 of the fastener 3 in the bone tissue as shown in phase (f).

Obviously, in the method as illustrated in FIG. 1, establishment of the press-fit (phase (c)) and establishment of the anchorage (phase (e)) are carried out after each other and independent from each other, wherein force F.2, which is applied to the anchoring element for the advancement thereof in the anchoring step (phase (e)) is counteracted by the fastener 3 and has the same direction as force F.1 which is needed for establishing the press-fit (phase (c)), i.e. it has no component in a direction opposite force F.1 and therefore cannot in any way weaken the press-fit of the graft or soft tissue through the fastener.

Depending on the cross section of the graft 1 in a non-impacted state, the step of impaction (phase (b)) can be omitted. Use of a tapering fastener or tapering distal fastener end may also render the impaction step unnecessary. Depending on the density of the bone tissue of the tunnel wall and on the desired strength of the anchorage, the step of reaming (phase (d)) may be omitted. Reaming is advisable for very dense bone tissue. If the reaming step is carried out, the anchorage achieved in step (e) will be deeper and will reach bone tissue which has not been compacted by the press fitting. However, a similar effect may be achieved by equipping the fastener with an axial groove extending from the distal fastener end to the outer mouth of passage 5. The guide tool 14 may be positioned on the proximal end of the fastener 3 before the reaming step or even before establishing the press fit, wherein in the latter case, the guide tool is used for forcing the fastener 3 into the opening instead of the push rod 11. Depending on the stroke of advancement of the anchoring element necessary for achieving the desired anchorage (phase (e)) and on the guidability of the anchoring tool 13, use of a guide tool 14 may be omitted.

It may be advantageous to use a guide wire for introducing the dilator 10 and/or the fastener 3 into the bone opening which necessitates in a per se known manner an axial channel or bore (centric or ex-centric) in the dilator 10 and/or the fastener 3. Experiments show that it is advantageous to provide the axial bore in the dilator 10 and/or fastener 3 as close as possible to the circumferential surface of the side which is to be facing towards the wall of the opening. Instead of the bore it is possible also to provide a groove (preferably undercut) along the circumferential surface of the dilator and/or the fastener for guiding these along the guide wire.

FIG. 1 shows the fastener introduced in the bone opening 2 with its proximal face being flush with the bone surface. This, of course, is not a condition of the method according to the invention. Without alteration to the fastener and the method it is possible also to introduce the fastener further into the bone, such that the proximal fastener end is buried in the bone, or less far, such that the proximal fastener end protrudes from the bone.

As already mentioned, the anchoring tool 13 is e.g. a vibrating tool (e.g. sonotrode connected to an ultrasonic transducer being e.g. part of an ultrasonic device such as an ultrasonic hand piece), which transmits ultrasonic vibration to the anchoring element 6 and is simultaneously pressed against the proximal face thereof or is rigidly fixed thereto and pressed against the closed distal end of the fastener 3 together with the anchoring element. In such a case it is advantageous to provide either on the anchoring element 6 or inside the inner cavity 4 energy directors (protruding points or edges) where liquefaction is desired. Such energy director for the fastener 3 and anchoring element 6 in the illustrated case is constituted by the tapering distal end of the anchoring element 6. Alternative embodiments of such energy directors are e.g. edges or points protruding into the inner cavity from the rim of the inner mouth of passage 5. Further embodiments of such energy directors are disclosed in the provisional U.S. application No. 61/259,383 (not published yet), whose disclosure in its entirety is enclosed herein by reference.

The anchoring tool 13 may also be equipped for transmitting rotational energy to the anchoring element being rigidly fixed thereto, wherein the heat required for liquefaction of the anchoring element material is in such a case produced by friction between the distal face of the rotating anchoring element and the non-rotating inner fastener surface. Alternatively, the anchoring tool 13 may be equipped for transferring electromagnetic energy (preferably in the visible or infrared frequency range) or electric energy to the anchoring element 6 or to the fastener 3, wherein either the anchoring element 6 or fastener regions in the vicinity of the anchoring element need to be equipped for transforming the transmitted energy into thermal energy by e.g. comprising light absorbing means or electric resistance means.

If the fastener 3 according to FIG. 1 is used for extra-graft fixation in a blind opening, it may be desirable to anchor it in addition to the anchorage in the circumferential wall of the opening also in the bottom wall of the opening or exclusively in the bottom wall of the opening (see also FIG. 26). In such a case, the fastener needs to be introduced into the blind bore such that it substantially touches or at least comes near the bottom wall of the opening and it needs to comprise at least one passage 5 connecting the inner fastener cavity 4 with a distal fastener face, which passage is provided in addition to or in place of the lateral passage 5 illustrated in FIG. 1. Such distal fastener surface being equipped for the fastener anchorage constitutes a fastener surface portion being separated from fastener surface portions equipped for pressing not as a circumferential sector (as above described for the surface comprising the lateral passage 5) but as an axial portion, as already mentioned further above.

The fastener 3 is made of a material which may or may not be biologically resorbable as known for fasteners according to the state of the art, which serve the same purpose. If the fastener is not to be resorbable it is e.g. made of a metal (e.g. titanium, titanium alloy, stainless steel), a ceramic material (e.g. aluminum oxide, zirconium oxide), a calcium phosphate, or of a polymer (e.g. thermoplastic, e.g. PEEK, possibly coated e.g. with an inner coating of titanium and an outer coating of hydroxyapatite). Although it seems advantageous to make the fastener of a material which is not liquefiable under the conditions of the anchoring process, experiments show that the fastener may also be made of a liquefiable material, even of the same material as the liquefiable material of the anchoring element. Good results have e.g. been achieved with fasteners made of titanium, or of polylactic acid (PLA) filled with Hydroxyapatite or calciumphosphates, in particular of PLLA filled with 60% tricalciumphosphate or PDLLA 70%/30% (70% L and 30% D/L) filled with 30% biphasic calciumphosphate, combined with anchoring elements of PLDLLA 70%/30% (70% L and 30% D/L), as available from Behringer as LR706.

Particularly in a case in which the graft (or natural soft tissue or corresponding artificial element) to be fastened is very heat sensitive it is preferable to use, at least for a fastener region which is to be situated in the vicinity of the graft, a material which has some heat insulating characteristics. If the graft to be fastened is less heat sensitive (e.g. artificial tissue replacement material) such precaution is not necessary. For such non-heat-sensitive tissue which in addition is sufficiently deformable it is even possible to provide passages 5 directed also to the side of the graft, wherein for the anchoring process these passages will be closed by the compacted graft and will not or hardly permit passage of the liquefied material (advantage: no specific rotational fastener orientation in the opening is needed).

The extra-graft fixation as illustrated in FIG. 1 can e.g. be achieved by providing a tunnel or blind bore of 8 mm diameter, a substantially cylindrical fastener of 7 mm diameter and a graft having a stitched end portion which passes easily through a bore of 7 mm diameter. Experiments show that substantially cylindrical fasteners with a tapering distal end, in particular with a hemispherical end as illustrated in FIG. 1 and with a circumferential surface of a roughness of not more than 10 µm depth give a good press-fit and can be introduced with reasonable forces, while fasteners with flat distal ends and/or a greater surface roughness seem to necessitate higher introduction forces but do not result in a better press fit. A stronger press-fit is achieved by using longer fasteners.

Figure 2:
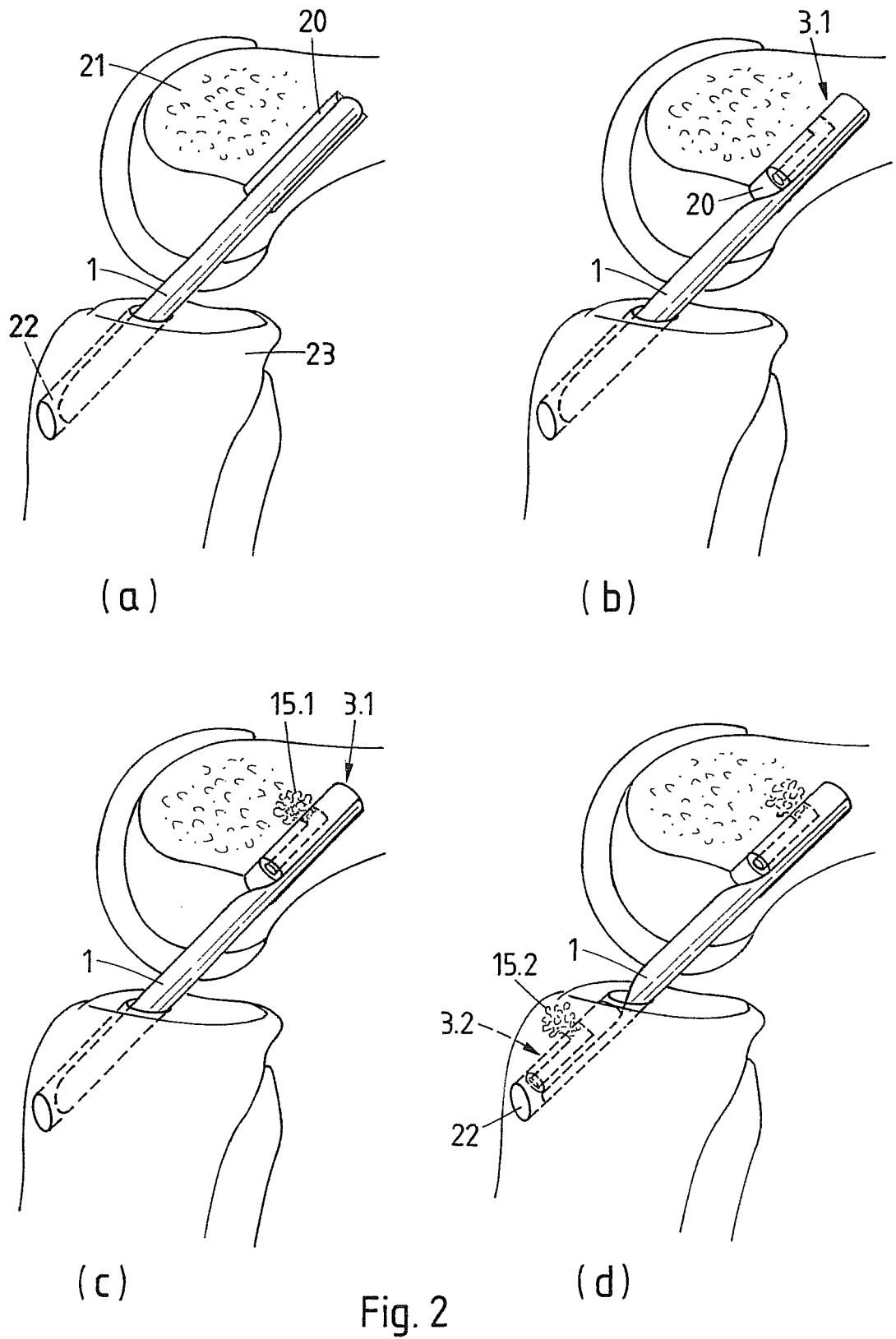
FIG. 2 shows four consecutive phases of an exemplary ACL replacement surgery using the method as shown in FIG. 1.

FIG. 2 shows in a schematic manner four consecutive phases (a) to (d) of an exemplary surgical procedure for replacing an anterior cruciate ligament (ACL) in a human knee, wherein the graft 1 used for the replacement comprises e.g. two terminal bone blocks and wherein one of these terminal bone blocks is fastened in a blind bore 20 in the femoral bone 21 and the other one in a tunnel 22 reaching through the tibial bone 23. The per se known procedure comprises a femoral and a tibial fixation process which can both be carried out using the method according to the invention as e.g. illustrated in FIG. 1.

In phase (a) the tibial tunnel 22 and the femoral blind bore 20 are provided and the graft 1 is positioned for the fixation processes. In phase (b) the femoral fastener 3.1 is press-fitted in the femoral blind bore 20. In phase (c) the femoral fastener 3.1 is anchored in the wall of the femoral blind bore 20 (anchorage 15.1). In phase (d) the tibial fastener 3.2 is press-fitted and anchored (anchorage 15.2) in the tibial tunnel 22.

FIG. 3 shows as mentioned already further above, the fixation of a stitched graft end 16 in bone opening 2 using a fixation method similar to the one illustrated in FIG. 1. The bone opening 2 is a tunnel and comprises a portion 2.1 of a larger cross section and a portion 2.2 of a smaller cross section, wherein the stitched graft end 16 and the fastener 3 are arranged in the tunnel portion 2.1 and the suture ends 17 extending from the stitched graft end 16 exit through the tunnel portion 2.2 and are e.g. used for tensioning the graft before compressing it with the dilator or introducing the fastener 3. The graft 1 comprising the stitched graft end 16 is e.g. a two-strand graft wherein the two strands are fixed to each other by a series of cross stitches around both lateral sides and made with one suture, the two suture ends 17 protruding from the stitched graft end. The graft 1 may also be a four strand graft being made by folding in two a two-strand graft with two ends being stitched in the named manner, the four-strand graft then comprising a fold end without suture ends and a stitched end with four protruding suture ends. The step of anchoring the fastener in the wall of the tunnel portion 2.1 is e.g. carried out as above described in connection with FIG. 1.

FIG. 4 shows the fixation of a stitched graft end 16 in a bone opening 2 being a blind bore, wherein the stitched graft end 16 is fixed to the fastener 3 preferably with the aid of the suture ends 17 protruding from the stitched graft end 16. This fixation is established before introduction of the graft end 16 and the fastener 3 in the opening and the two are introduced together into the opening 2 for establishing the press-fit. FIG. 3 shows the graft end 16 and the fastener 3 positioned in the bone opening 2. The step of anchoring the fastener 3 in the wall of the opening is established e.g. in the manner as illustrated in FIG. 1.

The fixation of a stitched graft end to the fastener 3 can e.g. be achieved, as illustrated in FIG. 4, by threading a first part of the suture ends 17 through the inner cavity 4 of the fastener 3, which for this purpose comprises an open distal end, and a second part of the suture ends 17 along the circumferential surface of the fastener 3 and providing a knot or other suitable suture retainer at the proximal fastener face for connecting the two parts of suture ends 17. The circumferential fastener surface and/or the inner fastener cavity may comprise an axially extending groove for accommodation of the suture ends. If the suture is heat sensitive and there is a risk of the suture to be damaged by the liquefied material inside the inner fastener cavity, it will be advantageous to provide at least one separate tunnel through the fastener for the suture (see also FIG. 19) It is also possible to equip the distal end of the fastener 3 with an eyelet or similar retention means to which the suture ends 17 protruding from the stitched graft end 16 can be fixed in a suitable manner before the graft end 16 and the fastener 3 are introduced in the bone opening 2 together. It is also possible of course to fix a non-stitched graft end to the fastener in a suitable manner.

FIGS. 5 to 9A/B show further exemplary embodiments of fasteners 3 together with adapted anchoring elements 6 and anchoring tools 13, wherein all the illustrated sets of fastener 3, anchoring element 6 and anchoring tool 13 are suitable for an anchoring step which is slightly different from the anchoring step illustrated in FIG. 1 but which are all suitable for the fixation applications as illustrated in FIGS. 1 to 4. FIGS. 5 to 9 illustrate the anchoring steps for extra-graft fixation but as discussed further below, their principle is applicable for intra-graft fixation also.

FIG. 5 shows an axial section of a fastener 3 which is press-fitted in a bone tunnel 2 for fastening a graft 1 in the bone tunnel. The fastener 3 is principally the same as the fastener illustrated in FIG. 1, but as passage 5 reaching from the inner cavity 4 to the outer fastener surface a plurality of openings is provided instead of the one slot-like fenestration according to FIG. 1. The anchoring element 6 is tube-shaped and sits loosely on the foot piece 25 of an extension 26 of the anchoring tool 13, which again is preferably a vibration tool. For the anchoring process, the extension 26 together with the anchoring element 6 is introduced into the inner cavity 4 of the fastener 3. The anchoring tool 13 is then activated and the anchoring element 6 is held and advanced against the foot piece 25 by applying a corresponding force F.2 to a counter element 27 acting on the proximal face of the anchoring element 6. The thermoplastic material comprised by the anchoring element 6 is liquefied at the distal face of the anchoring element 6 where it is in contact with the vibrating foot piece 25. By corresponding positioning of the interface between foot piece 25 and anchoring element 6 the liquefied material is made to flow through passage 5 into the tunnel wall, wherein this interface is displaced for subsequent anchoring processes through different passages 5. FIG. 5 shows the set-up during the anchoring process, wherein the anchoring material has already been forced through a distal and a middle passage 5, wherein the named interface is still positioned at the middle passage, and wherein a proximal passage is still free from the anchoring material.

With the combination of anchoring element 6, anchoring tool 13 and counter element 27 as shown in FIG. 5, advancement of the anchoring element 6 may also be effected by pulling the foot piece 25 towards the proximal face of the fastener 3, while keeping the counter element 27 substantially stationary, e.g. pressed against the bone surface. It is possible also to reverse the functions of anchoring tool and counter tool, i.e. to vibrate the counter element 27 and to use the foot piece 25 as counter element. Furthermore, for the fastener anchoring as illustrated in FIG. 5, as already mentioned for the fastener anchoring according to FIG. 1, it is also possible to use energy types other than vibration energy. Further embodiments and details of the principle of the anchoring process as illustrated in FIG. 5 are described in the publication WO-2009/132472, whose disclosure in its entirety is enclosed herein by reference. In an alternative embodiment of the combination of anchoring element 6 and anchoring tool 13 as illustrated in FIG. 5 the tube-shaped anchoring element 6 constitutes the consumable element in a dispenser-like device and is liquefied at a distal device end in a similar way as shown in FIG. 5. Such dispenser devices are described in the publication WO-2010/127462 whose disclosure in its entirety is enclosed herein by reference.

It is obvious that in the fixation method as illustrated by FIG. 5 the force F.2 needed for advancing the anchoring element 6 is not counteracted by the fastener 3. Therefore, this force cannot weaken the press-fit of the fastener, whatever its direction may be, and it allows use of a fastener not having a closed distal end and introducing the anchoring element from either the proximal or distal fastener end.

FIG. 6 is an axial section of a further set of fastener 3, anchoring element 6 and anchoring tool 13, wherein the fastener 3 is shown in the bone opening 2 before the anchoring step, i.e. press-fitted between the graft 1 and the opposite wall of the bone opening 2. Other than described above, the fastener 3 does not comprise an inner cavity and passages connecting the inner cavity to the outer fastener surface (as illustrated in FIGS. 1 to 5) but instead, for guiding the liquefiable material comprised by the anchoring element 6 from a proximal fastener face to the anchoring portions of the circumferential fastener surface, the fastener 3 comprises at least one groove 30 which extends from the proximal fastener face towards the distal fastener end and may have a slightly undercut cross section. The anchoring element 6 is adapted to substantially fill this cross section and to protrude slightly from it and it is pushed into the groove 30 of the press-fitted fastener 3 from the proximal fastener face with the aid of anchoring tool 13. Therein the anchoring element 6 is advantageously rigidly attached to the distal end of the anchoring tool 13, such that vibration energy (or other type of energy) is transmitted substantially loss-free into the anchoring element and liquefaction occurs where the anchoring element comes into contact with the bone tissue of the wall of the bone opening and possibly also where the anchoring element comes into contact with the inner surface of groove 30. Groove 30 may comprise a rough or otherwise suitably structured inner surface such that liquefaction and re-solidification of the anchoring material may result in a positive-fit connection not only with the bone tissue of the bone wall, but at the same time also with the fastener surface inside groove 30.

If a fastener 3 according to FIG. 6 comprises more than one groove, anchoring of the fastener necessitates more than one anchoring step, wherein these anchoring steps may be executed in succession using one and the same anchoring tool for all the steps, or wherein the anchoring steps may be executed simultaneously using a fork-shaped anchoring tool.

FIG. 7 is an axial section through a further embodiment of a set of fastener 3, anchoring element 6, and anchoring tool 13, which set further comprises a guide tool 14 and is suitable for an anchoring process similar to the one described in connection with FIG. 6. The set is illustrated with the fastener 3 press-fitted together with a graft 1 in a bone opening 2, the set being ready for the anchoring step. The guide tool 14 comprises an axial through bore having a cross section adapted to the cross section of the anchoring element 6 and to the distal end of the anchoring tool 13, wherein the through bore is angled relative to a tool axis by an acute angle of 2 to 10°, preferably 3°. As already illustrated in FIG. 6, for the anchoring step, the anchoring element 6 is to be advanced from the proximal fastener face along a groove 30 provided on the fastener side opposite the graft 1. Other than shown in FIG. 6, the groove 30 according to FIG. 7 comprises a wider entrance portion 30.1 and a narrower distal portion 30.2, wherein the distal portion preferably has a closed end. In preparation of the anchoring step, the guide tool 31, which may also serve for forcing the fastener into the bone opening 2, is positioned on the proximal fastener face with the distal mouth of its through bore being aligned with the entrance portion of groove 30. The anchoring element 6 and the distal end of the anchoring tool 13 are positioned in the through bore of the guide tool 31, the distal end of the anchoring element being supported in the entrance portion 30.1 of groove 30. During the anchoring process the anchoring element 6 is advanced into groove 30, wherein the angled position of the anchoring element 6 as illustrated in FIG. 7 as compared with the axial position as shown in FIG. 6 forces the material of the anchoring element more against the wall of the bone opening and therewith enhances liquefaction and penetration into the bone tissue. This effect is amplified by the groove 30 having a closed end.

Experiments show, that anchoring a fastener having a diameter of 8 mm and a distal groove portion 30.2 of a semicircular cross section of 1.5 to 2 mm radius using a pin-shaped anchoring element of 3.5 mm diameter gives good results.

FIG. 8 is an axial section through a further embodiment of a set of fastener 3, anchoring element 6, and anchoring tool 13, the fastener 3 and a graft 1 being shown press-fitted in a bone tunnel before the anchoring step. The anchoring element 6 is constituted by an integrated central part of the fastener 3 which is e.g. fully made of the liquefiable material, wherein this material may comprise filler compounds (whiskers, fibers, particles) whose concentration may decrease in a direction from the circumferential fastener surface towards the central fastener region constituting the anchoring element 6. The fastener comprises an inner cavity 4 in the form of an axial channel and at least one passage 5 connecting the channel with an anchoring sector of the circumferential fastener surface. The channel preferably has a wider proximal portion 32 and a narrower distal portion 33, and the anchoring tool 13 adapted to the fastener 3 has at least a distal portion which is adapted to the wider channel portion 32 for being guided therein. The anchoring element 6 is constituted by the fastener portion surrounding the distal (narrower) channel portion 33 and is advanced and liquefied by forcing the anchoring tool 13 from the wider channel portion 32 into the narrower channel portion thereby pressing the liquefied material through the passages 5 to the outer fastener surface. Further embodiments and details of the fastener and anchoring process as illustrated in FIG. 8 are described in the publication US-2008/262517 (Stryker Trauma GmbH), whose disclosure in its entirety is enclosed herein by reference.

FIG. 9A is an axial section through a further embodiment of a set comprising a fastener 3, an anchoring element 6 and an anchoring tool 13, wherein the fastener 3 is shown press-fitted with a graft 1 in a bone opening 2, on the left hand side of the figure before the anchoring step and on the right hand side of the figure after the anchoring step. The embodiment may be considered to be a combination of the embodiment according to FIGS. 6 and 8, i.e. to comprise at least one anchoring element 6 integrated in the fastener 3 which may fully consist of the anchoring material, and which possibly contains a filler having possibly a lower concentration where the material is to be liquefied than in other areas, as discussed in connection with FIG. 8. However, other than shown in FIG. 8 the anchoring element 6 or the material to be liquefied respectively is not situated in a central area of the fastener but at the circumferential surface thereof, as discussed in connection with FIG. 6. The anchoring tool 13, which preferably has a tapering distal end, is forced into the fastener material parallel to the wall of the bone opening in the surface region of the liquefiable material. When after completion of the anchoring step the anchoring tool is removed, it leaves a void 15' between a central area of the fastener and the anchorage 15 in the bone wall, which is connected to the rest of the fastener beside the void 15' as clearly seen in FIG. 9B (cross section through the anchored fastener 3).

FIGS. 10 to 17 show various embodiments of fasteners 3 based on the fastener principle (fastener with inner cavity 4 connected to circumferential fastener surface and anchoring element adapted to fit into the inner fastener cavity) as illustrated in FIGS. 1 to 5 but differing in form. All these fasteners 3 are applicable in the fixation methods and applications as illustrated in FIGS. 1 to 5.

Figure 10:
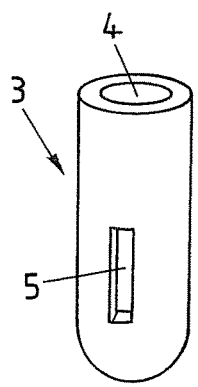

FIG. 10 is a three-dimensional illustration of a very simple fastener 3 which has the form of a circular cylinder with a rounded distal end. It comprises an inner cavity 4 and one only slot-shaped passage 5 connecting the inner cavity 4 with the circumferential fastener surface.

Figure 11:
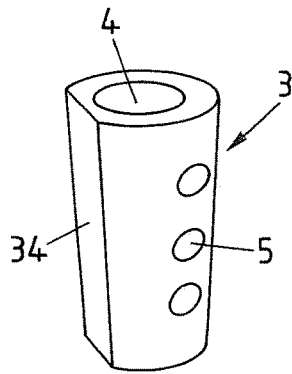
Figure 12:
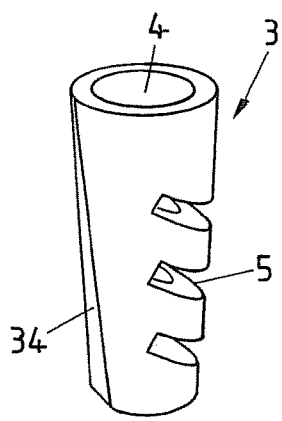
Figure 13:
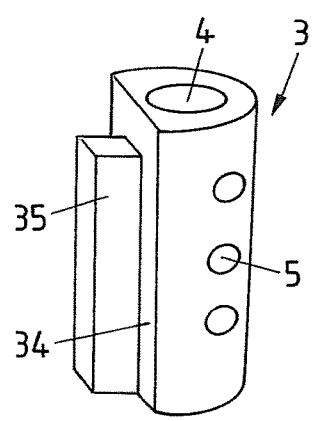

FIGS. 11 to 13 are three-dimensional illustrations of further fasteners 3 similar to the fastener of FIG. 10. These fasteners comprise on the right side (anchoring sector of the circumferential fastener surface) passages 5 connecting the circumferential fastener surface with the inner cavity 4. The passages are in FIGS. 11 and 13 two axially extending rows of bores (one row visible), in FIG. 12 one axially extending row of substantially circumferentially extending slots. The fasteners of FIGS. 11 to 13 further comprise on the left side (pressing sector 34 of the circumferential fastener surface) a flattened or concave sector forming a shallow groove for accommodating the graft to be fastened. In addition, the fastener of FIG. 13 comprises an axially extending ridge 35 in the center of the pressing sector 34 which ridge serves for holding a folded graft (not shown) which is folded over the distal end of the ridge 35 for being forced into the bone opening together with the fastener 3 in a way similar to the one discussed in connection with FIG. 4.

Figure 14:
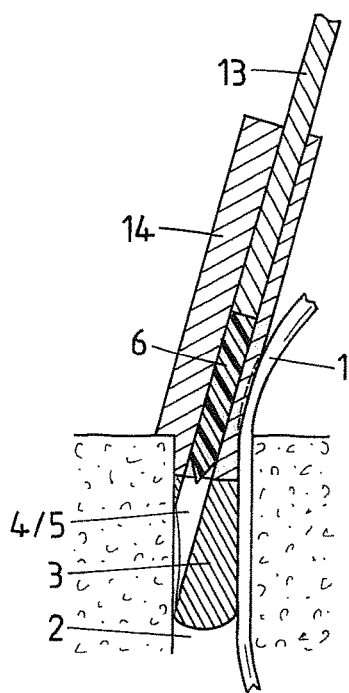

FIG. 14 is an axial section of a further fastener 3 the fastener being illustrated press-fitted with a graft 1 in a bone opening and the figure further illustrating the anchoring element 6, the anchoring tool 13 and a guide tool 14 similar to the guide tool as discussed in connection with FIG. 7, the whole set being ready for the anchoring step. The fastener 3 comprises at least one channel 4/5 (combination of inner cavity 4 and passage 5) extending at an angle to the fastener axis. The at least one channel 4/5 comprises a first mouth in the proximal fastener face which serves for introduction of the anchoring element 6 and possibly a distal end of the anchoring tool and a second mouth in the circumferential surface of the fastener, which serves for pressing the anchoring material against the bone wall of the bone opening, wherein the anchoring material is either liquefied within the channel 4/5, which for this purpose preferably comprises inner energy directors, or at the interface with the bone wall.

Figure 15:
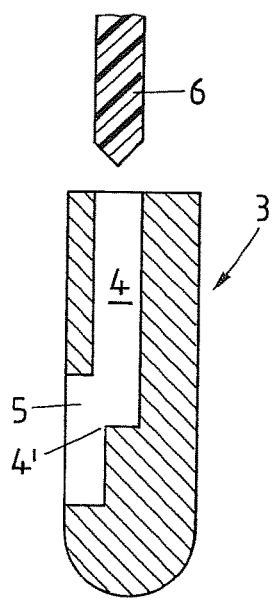

FIG. 15 is an axial section of a further fastener embodiment which comprises an inner cavity 4 and a passage 5 wherein the inner cavity 4 is arranged non-coaxial with the fastener axis and comprises a step 4' or a corresponding bend which is able to divert the anchoring element 6 towards the passage 5. This arrangement results in an effect of forcing the anchoring material towards the fastener surface or the bone wall respectively in a similar way as discussed in connection with FIG. 7.

Figure 16:
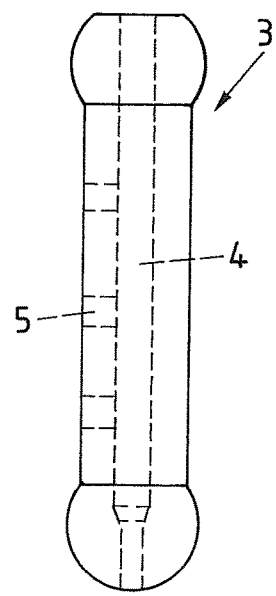

FIG. 16 is a lateral view of a further fastener 3 comprising an inner cavity 4 and passages 5 connecting the inner cavity with the circumferential fastener surface. The fastener comprises distal and proximal end regions having a greater cross section than a middle region. The two end regions are in particular spherical. Experiments show that the fastener according to FIG. 16 provides a press-fit as good as a cylindrical fastener but can be introduced into the bone opening with less force.

FIG. 17 is a three dimensional illustration of a distal end of a fastener 3, which is advantageous for being introduced into the bone opening beside a graft, wherein the graft is positioned at the one side of the fastener 3 which is in FIG. 17 the left hand side of the fastener. The distal fastener end is tapering on this graft side for preventing graft damage on introduction of the fastener beside the graft in the bone opening. The distal fastener end is tapering on the non-graft side (right hand side in FIG. 17) also but less, wherein the distal mouth of an axial through bore through the fastener for accommodation of a guide wire is situated in there. As already mentioned in connection with FIG. 1, it is advantageous to position the through bore 37 and therewith the guide wire ex-centrically and as close as possible to the anchoring side of the fastener. The through bore 37 or a proximal section thereof may or may not serve as inner cavity 4 as described for the fastener embodiments according to e.g. FIG. 1 or 5.

FIGS. 18 to 22 illustrate ways in which in a fixation according to the invention the fastener 3 can be adapted to the graft 1 and the bone opening 2. The illustrated fasteners are all suitable for extra-graft fixation and are partly based on the fastener principle as illustrated in to FIGS. 1 to 5 (fastener with inner cavity and at least one passage connecting the cavity to the circumferential fastener surface and anchoring element adapted to be positioned in the inner cavity), and partly on the fastener principle as illustrated in FIGS. 6 and 7 (fastener with at least one surface groove running in axial direction and anchoring element adapted to be advanced in the groove). Adaptation to the fastener principles according to FIGS. 8 and 9 (anchoring element integrated in fastener and anchoring material forced from the fastener by forcing the anchoring tool into the fastener) can be easily envisaged by one skilled in the art knowing the present disclosure without departure from the invention.

FIG. 18 is a cross section through the fixated fastener 3 and graft 1, wherein the fastener 3 has a substantially round cross section smaller than the also substantially circular cross section of the opening. The graft 1 which needs to be easily compressible is compacted in a narrow slot between the wall of the opening and the circumferential surface of the fastener 3 opposite the anchorage 15 of the fastener in this wall. Exemplary dimensions for the fastener 3, graft 1 and bone opening according to FIG. 18 are: opening diameter of 8 mm, fastener diameter 7 mm, graft (e.g. with stitched end) sized to easily pass through a 7 mm bore.

FIG. 19 is a top view of a fastener 3 comprising an at least partly concave pressing sector 34 forming a very shallow, axially extending groove for accommodating the graft. The anchoring sector of the fastener 3 (opposite the pressing sector 34) is substantially circular and has the same radius as the bone opening 2 provided for the fastener. The fastener 3 may further comprise an axial through bore 37 adapted to be used for advancing the fastener along a guide wire and/or for threading suture ends protruding from a stitched graft end portion through the fastener as above discussed in connection with FIGS. 4 and 17. Exemplary dimensions for the fastener 3 according to FIG. 19 and a graft and bone opening adapted therewith are e.g.: opening diameter 8 mm, radius of anchoring sector of fastener: 4 mm, area ratio of cross sections of fastener and opening: the same as for the fastener of FIG. 18, graft (e.g. with stitched end): sized to easily pass through a 7 mm bore.

FIG. 20 is a cross section through a fastener 3 and a graft 1 anchored in a bone opening 2. The fastener comprises a flattened pressing sector 34 as discussed in connection with FIGS. 11 to 13 wherein the graft 1 is compressed in the gap between this pressing sector 34 and the wall of the opening and wherein the exact form of the pressing sector 34 is adapted to the form of the graft and to its compressibility.

In FIG. 21, the fastener 3 has again a substantially circular cross section which is considerably smaller than the also substantially circular cross section of the opening 2. The circumferential surface of the fastener 3 is pressed into the graft 1 which is not very deformable, while on both sides of the fastener 3 and possibly of the graft 1 the bone opening 2 remains empty, unless means are provided on the fastener 3 for liquefied anchoring material of the anchoring element to flow into this empty space in addition to the penetration of the bone wall of the opening.

In FIG. 22 the graft 1 is only little compressible and deformable and has e.g. a substantially circular cross section. A shallow groove (pressing sector 34) is provided in the fastener for accommodating the graft 1.

FIGS. 18 to 20 are rather theoretical as they ignore the fact that in reality the bone tissue around the bone opening is compressed by the forces acting on the latter on introduction of the fastener and by the press-fit achieved through this introduction such that the cross section of the bone opening is deformed, the degree of this deformation being dependent of the mechanical properties of the bone tissue.

FIG. 23 illustrates an embodiment of the method according to the invention in which the opening 2 in the bone is pretreated with a first portion of liquefiable material to be liquefied in situ and made to penetrate the trabecular structure of the wall of the opening 2 and/or cavities provided therein and, on re-solidification to form a sort of composite layer 40 in which the liquefiable material and the bone tissue are connected to each other in a positive fit connection. Preferably this pretreatment step is carried out such that the cross section of the opening 2 remains substantially unchanged. Following the pretreatment step, the fixation is carried out exactly as described for e.g. the method as illustrated in FIG. 1 or 5, wherein, in the anchoring step a second portion of liquefiable material comprised by the anchoring element is liquefied in situ and made to get into contact with the first portion and therewith to be welded thereto. The first and second portions of liquefiable material preferably comprise the same material having thermoplastic properties but may also comprise different such materials which however need to be chosen to be capable of forming a welded connection 41 under the conditions of the anchoring step. Adaptation of the method illustrated in FIG. 23 to other fastener principles as illustrated in FIGS. 5 to 9 is easily possible for one skilled in the art and in knowledge of the present disclosure without departure from the scope of the invention.

The pretreatment step is e.g. carried out in the same way as described for the anchoring step of the method according to FIG. 5 wherein no fastener is positioned in the bone opening 2 and the cross sections of the foot piece and the anchoring element are only very slightly smaller than the cross section of the bone opening. Further exemplary methods for carrying out the pretreatment step are described in the publication WO 2009/141252 (Nexilis) and WO-2010/045751, the entire disclosure of both being enclosed herein by reference.

For not impairing bone tissue regenertation between the graft and the bone tissue of the wall of the bone opening, it may be advantageous to restrict the above described pretreatment to the anchoring side of the fastener. Such selective pretreatment of the wall of a bone opening is described in the above mentioned publication WO-2010/045751 in connection with FIG. 8.

FIG. 24 illustrates an exemplary embodiment of an expandable fastener which is suitable for an extra-graft fixation and an anchoring step as described for the method as illustrated in FIGS. 1 to 5. The fastener comprises a slotted sleeve part 3a and a spreader part 3b, which is e.g. screw-shaped. The sleeve part 3a is open at least proximally and comprises at least one axial slot 43 or a plurality of such slots which are arranged facing one only side of the sleeve part 3a (anchoring sector). The spreader part 3b comprises an axial channel 44 and passages 45 connecting the axial channel 44 with the circumferential surface of the spreader part 3b. The spreader part 3b is adapted to the sleeve part 3a such that on introduction of the spreader part 3b into the sleeve part 3a the sleeve part is radially expanded and the slot(s) 43 are opened or widened. The opening provided in the bone is adapted to the sleeve part 3a such that the latter can be introduced into the opening after or together with the graft without the need of a substantial force and such that introducing the spreader part 3b into the positioned sleeve part causes enough expansion of the sleeve part for achieving a sufficient press-fit. The press-fit is produced by positioning the sleeve part 3a between the bone wall of the opening and the graft with the slot(s) 43 facing the bone wall and by then screwing the spreader part 3b into the sleeve part 3a. The anchoring step is carried out e.g. as described further above in connection with FIGS. 1 to 5 wherein the liquefiable material is liquefied in the axial channel 44 of the spreader part 3*b* and made to flow through the passages 45 and the slots 43 to get into contact with the wall of the opening. As there are slots 43 only in an anchoring sector of the sleeve part, the spreader part 3*b* may comprise passages 45 all round, wherein such passages eventually positioned in the pressing sector will be kept closed by the sleeve part.

One skilled in the art knows other embodiments of expandable fasteners which he can adapt easily to be suitable for the method according to the invention as illustrated in any one of the FIG. 1 to 9 or 23.

FIG. 25 illustrates a further embodiment of the method according to the invention in which a graft 1 is fastened in a bone opening 2 (extra-graft fixation in e.g. a bone tunnel). The left hand side of FIG. 25 shows the fastener 3 and the graft 1 press-fitted in the tunnel (assumed introduction direction from the top of the drawing) with the anchoring element 6 ready for the anchoring process (e.g. rigidly fixed to the anchoring tool 13) and on the right hand side the press-fitted and anchored fastener 3, i.e. the finished fixation. The fastener 3 used in this method comprises again pressing surface portions and anchoring surface portions, wherein the different portions are arranged along the fastener axis (not like in the previous Figs. sectors arranged around the fastener circumference). In other words, the pressing surface portion extends all around the fastener with the anchoring surface portion arranged proximally and possibly also distally thereof. The fastener 3 may have an even proximal face but preferably has a sloping or stepped proximal face oriented to leave more of the bone wall free than of the graft surface, wherein selected portions of the proximal fastener face may be rough or otherwise suitably structured. The anchoring element 6 has a cross section which may be substantially the same as the cross section of the fastener 3 and is pushed into the space between the bone wall of the opening and the graft 1 towards the proximal fastener face and at the same time the anchoring tool 13 is vibrated (or activated for transmitting other energy to the anchoring element). Therewith the liquefiable material is liquefied at least where in contact with the bone wall of the tunnel but preferably also where in contact with the proximal face of the fastener 3 and will therewith provide a proximal anchorage for the fastener 3 in the bone wall. There will be no or hardly any liquefaction of the liquefiable material where it is in contact with the graft, as the graft, contrary to the bone wall of the opening, is mostly soft and cannot provide energy directors for initiating such liquefaction.

For fully preventing friction and transfer of thermal energy between the anchoring element 6 and the graft 1 it may be advantageous to use in the method as illustrated in FIG. 25, an anchoring element 6 and advantageously an anchoring tool 13 of a cross section which corresponds to only a part of the fastener cross section (e.g. semi-circular cross section for anchoring element and anchoring tool and substantially circular fastener cross section) and to introduce the anchoring element 6 into the bone opening 2 beside the graft such that anchoring element 6 and graft 1 do not touch or at least not press against each other.

If desired, the distal anchorage using anchoring element 6.1 is effected in exactly the same way as the proximal anchorage.

As detailed further above, it is advantageous to advance the anchoring element in the same direction as the fastener 3 was forced into the tunnel for making sure that the anchoring process can in no way weaken the press-fit achieved by forcing the fastener into the tunnel. Therefore, if distal anchoring is desired too, it will be advantageous to first effect the proximal anchorage (anchoring element 6) and then the distal anchorage (anchoring element 6.1).

The anchoring elements 6 and 6.1 may, as above described, have a substantially similar cross section as the fastener 3. However, this is not a necessity. The anchoring elements may e.g. further comprise grooving edges extending axially or reaming structures for grooving or reaming the walls of the opening while the anchoring element is advanced into the opening. Furthermore, the opening may be provided to be e.g. wider in the area in which the anchoring element is to be positioned than in the area in which the fastener is to be positioned.

FIG. 26 illustrates fixation (extra-graft fixation) of the end of a graft 1 in a blind opening with the aid of a fastener 3 comprising a proximal surface portion equipped for pressing and a distal surface portion equipped for anchoring. The principle of the anchoring process is the same as illustrated in FIGS. 1 to 4 with the difference that the fastener 3 is forced into the opening 2 preferably beyond the end of the graft to substantially get into contact with the bottom wall of the opening 2. The fastener 3 is then anchored laterally (anchorages 15L) and/or distally (anchorage 15D).

FIGS. 27 to 36 illustrate intra-graft fixations according to the invention. The principle of such intra-graft fixation is the same as above discussed for extra-graft fixation which means in particular that all anchoring principles described above for extra-graft fixation are applicable also for intra-graft fixation independent on whether they are specifically discussed below or not.

FIGS. 27 to 29 are cross sections through fasteners 3 applicable for intra-graft fixation in a bone opening being a tunnel with a constant or non-constant cross section or being a blind bore. The fasteners according to FIGS. 27 and 28 are applicable for grafts with two strands (or four strands separated in two pairs) and therefore comprise two pressing sectors 34, which are preferably situated on opposite fastener sides. A distal end of these fasteners is preferably equipped with a transverse groove for accommodation of the graft end at which the graft is e.g. folded. The fasteners according to FIGS. 27 and 28 are anchored in the wall of a bone opening with the aid of an anchoring element which is introduced in an inner fastener cavity 4, the liquefied material being forced through passage(s) 5 against the bone wall, wherein according to FIG. 27 passage(s) 5 are arranged on one fastener side only (one anchoring sectors only), according to FIG. 28 on opposite fastener sides (two opposite anchoring sectors). The fastener according to FIG. 27 further comprises an axial through bore 37 adapted for use of a guide wire and/or for threading a part of suture ends protruding from stitched graft ends through it as discussed in connection with FIG. 4.

FIG. 29 illustrates the same fastener principle as FIGS. 27 and 28 but is applicable for a four-strand graft, the four strands being separated from each other and accommodated in four pressing sectors 34, which are arranged around the fastener 3 e.g. in a regular pattern, mouths of passages 5 (anchoring sectors) being arranged between the pressing sectors 34. The fastener 3 according to FIG. 29 is preferably used for a graft comprising two folded strands and comprises at its distal end preferably two crosswise arranged transversal grooves each one for accommodating one of the two stand folds.

FIGS. 30 to 33 are three-dimensional illustrations of fasteners having a cross section similar to the one shown in FIG. 27 or 28. These fasteners differ from each other and from the fasteners illustrated in FIGS. 27 and 28 in the design of the pressing sectors, which according to FIG. 30 comprise retention means in the form of transversal ribs 38, while according to FIGS. 31 to 33 the fastener surface of the pressing sectors is substantially smooth. The shallow grooves constituting the pressing sectors 34 have a constant cross section along the fastener length for the fasteners 3 of FIGS. 30 and 31 and they have a decreasing depth and width towards the distal fastener end for the fastener of FIG. 32 and towards the proximal fastener end for the fastener of FIG. 33. Comparative experiments with the fasteners according to FIGS. 30 to 33 show that the fastener according to FIG. 31 achieves the best press-fit.

FIGS. 34A and 34B illustrate a set of fastener 3, anchoring elements 6 and anchoring tools 13 which are suitable for an intra-graft fixation of a graft 1 comprising two strands (or more than two strands separated in a pair of strand groups) in a bone tunnel or blind opening, in particular fixation of a graft 1 which is folded over the fastener 3 and is forced into the tunnel or blind opening together with the fastener 3. The fixation achieved with the set as illustrated in FIGS. 34A and 34B is based on the anchoring principle as illustrated in FIG. 6 or 7.

FIG. 34A is an axial section through the complete set before fixation, FIG. 34B comprises two cross sections through the fastener 3 and the graft 1 before fixation (above) and when the fixation is completed (below).

The fastener 3 according to FIGS. 34A and 34B comprises two surface sectors equipped for pressing and two surface sectors equipped for anchoring, the different sectors alternating around the fastener circumference. The pressing sectors 34 comprise shallow axial grooves which may end distally in a distal transversal groove 52 in which the folded end of the graft is accommodated. The anchoring sectors are equipped like the anchoring sector of the fastener according to FIG. 6 or 7. The fastening process for the fastener is substantially the same as the one described in detail in connection with FIGS. 6 and 7 and therefore reference is made to the corresponding part of the description further above.

FIGS. 35A and 35B show an intra-graft fixation for fastening a double-strand graft in a bone opening 2 (tunnel or blind opening), the fixation including a proximal anchorage similar to the proximal anchorage shown in FIG. 25 for an extra-graft fixation. FIG. 35A shows the process in an axially sectioned bone opening, FIG. 35B in a cross section through the anchoring element 6, wherein in both Figs. the left hand side shows the situation before the proximal anchorage is effected and the right hand side shows the finished fixation. The fastener 3 is press-fitted and possibly laterally anchored in the circumferential wall of the opening 2 (lateral anchorage 15L) using any of the methods as illustrated in previous Figs. Then the proximal anchoring element 6 which has a similar cross section as the fastener 3 and may have the form of a frustum is advanced into the opening 2 and pressed against the proximal face of the fastener using a suitably adapted anchoring tool 13, therewith achieving anchorage in the wall of the bone opening 2 proximal to the fastener 3 and possibly also in the proximal fastener face. As discussed further above in connection with FIG. 25, it is possible to effect a similar anchorage (not shown) on the distal fastener side once the proximal anchorage is made and prevents weakening of the press fit through the force necessary for advancing the distal anchoring element using a force which has a direction opposite to the direction of the force used for effecting the press-fit.

All fasteners illustrated in the FIGS. 1 to 34 are substantially cylindrical or slightly conical and imply to have substantially circular cross sections (not regarding grooves provided in the anchoring sectors of the fastener surface for guiding an anchoring element and flat or concave forms in the pressing sectors 34 provided for retaining the soft tissue or graft strands to be fastened). Although this will be the most preferred fastener form as it is suitable for being introduced in a drilled opening having a simple cylindrical form, this is not a condition for the invention. All the fasteners may have any cross section (e.g. oval, rectangular, polygonal) and fit into an opening of a corresponding cross section and they may taper continuously or stepwise towards the distal end and fit in a continuously or step-wise tapering opening.

FIG. 36 illustrates an example of intra-graft fixation (cross section through anchored fastener 3 and double strand graft 1) in a non circular bone opening using a fastener 3 having a non circular cross section. Therein the bone opening is e.g. provided by punching and has an elongated cross section and of two graft strands one is press-fitted in one end of the elongated cross section of the opening, the other strand in the other end, the fastener 3 being positioned and anchored (anchorage 15) in the center of the elongated cross section. The cross section of the opening may be e.g. oval or rectangular (with rounded edges) and it may be curved as illustrated, or substantially straight, in particular it may be adapted to the anatomical characteristics of the fixation site. The fixation as illustrated in FIG. 36 is e.g. applicable for ACL surgery and allows very good reconstruction of the natural situation regarding the foot print of the fixation, which allows adaptation to specific anatomical situations and crossing of the two strands within the knee joint as in the natural joint. While according to the state of the art, the elongated foot print can only be achieved with fixation in two separate bores, which require a minimal distance from each other, the fixation according to FIG. 36 can be realized in a considerably smaller space and is therefore e.g. easily possible in the knee of a female patient.

FIGS. 37, 38A/B and 39A/B/C illustrate further sets of fastener 3, anchoring element 6, anchoring tool 13 and guide tool 14, wherein the guide tool 14 is suitable not only for guiding the anchoring tool 13 and possibly the anchoring element 6 during the anchoring progress, but also for forcing the fastener into the bone opening preferably along a guide wire 60 for establishing the press-fit of graft 1 and anchor 3 in the bone opening 2. The illustrated sets are suitable for extra-graft fixation but can easily be adapted for intra-graft fixation.

FIG. 37 shows in axial section a fastener 3 and a graft 1 press-fitted in a bone opening 2, wherein the fastener is suitable for an anchoring process as illustrated e.g. in FIG. 1 or FIG. 5. Also shown is a guide wire 60 and a guide tool 14, the guide wire 60 extending through the inner cavity 4 of the fastener, which inner cavity 4 for this purpose comprises a distal end portion and mouth with a cross section adapted to the cross section of the guide wire 60. The inner cavity 4 is e.g. eccentrically positioned on the anchoring side of the fastener 3, which facilitates introduction of the fastener in the bone opening along the guide wire 60. The guide tool 14 is shaped e.g. for manipulation by hand and it comprises a distal end with a cross section adapted to the proximal cross section of the fastener 3, i.e. the guide tool 14 comprises an axial through bore adapted to continue the inner cavity 4 of the fastener in a proximal direction and it further comprises means for holding the fastener preferably with a push-on connection, e.g. protrusion 62, which fits into a corresponding depression of the fastener 3. The set further comprises an anchoring element 6 which is pin-shaped and adapted to be introduced through the axial bore of the guide tool 14 into the inner cavity 4 of the fastener 3, and an anchoring tool 13, whose distal end portion is also adapted to be introduced through the axial bore of the guide tool 14. Anchoring element and anchoring tool are not shown in FIG. 37.

Using the set according to FIG. 37, the fixation process comprises the following steps: introducing the graft 1 and the guide wire 60 into the bone opening; attaching the fastener 3 to the guide tool 14; introducing the proximal end of the guide wire 60 into the distal mouth of the inner cavity 4 and forcing the fastener 3 along the guide wire 60 into the opening, by e.g. using an impaction tool being applied to the proximal end of the guide tool 14 or possibly, for protecting the proximal end of the guide wire 60, being applied to a cannulated interface piece 63 positioned on the proximal face of the guide tool 14; removing the interface piece 63 and the guide wire 60; introducing the anchoring element 6 and the anchoring tool 13 through the axial bore of the guide tool 14 towards the fastener; transmitting energy through the anchoring tool 13 to the anchoring element 6 for the anchoring process; stopping the energy transmission and removing the anchoring tool 13 and the guide tool 14.

If the fastener 3 comprises a separate axial bore for the guide wire, as shown e.g. in FIGS. 19 and 27, the guide wire may be left in this bore during the anchoring step and may be removed together with the anchoring tool and the guide tool. In such a case it is possible also for the inner cavity to be angled relative to the through bore for the guide wire for an anchoring process similar to the one illustrated in FIG. 14.

FIGS. 38A and 38B illustrate a further set comprising a fastener 3, an anchoring element 6, an anchoring tool 13, and a guide tool 13 in an axial section (FIG. 38A) and a cross section (FIG. 38B), wherein the anchor is press-fitted together with a graft 1 in a bone opening 2 and the set is ready for the anchoring step. The set is suitable for introduction of the fastener 3 into the bone opening 2 along a guide wire 60 and for anchoring the fastener 3 using a method similar to the one illustrated in FIG. 25. The fastener 3 comprises an anchoring element 6, which is attached on the proximal face of the fastener and has a cross section constituting a part of the fastener cross section, e.g. substantially semicircular cross section of anchoring element 6 and substantially circular cross section of fastener 3. The fastener 3 and the anchoring element are preferably made as one piece and consisting of the same thermoplastic material At the transition from the anchoring element 6 to the fastener 3, the anchoring element comprises a reduced cross section, e.g. through a groove 70 running along the circumferential surface between anchoring element 6 and fastener 3. The cross section reduction serves for concentrating the vibration energy transmitted by the anchoring tool to the anchoring element 6 such that liquefaction of the anchoring element starts in the region of the cross section reduction, i.e. on the distal side of the anchoring element or on the proximal face of the fastener respectively. The fastener 3 and possibly the anchoring element 6 further comprise an axial through bore for accommodation of the guide wire 60.

The cross section of the anchoring tool 13 is adapted to the cross section of the anchoring element 6. The guide tool 14 comprises an axial bore for the guide wire 60 and a channel adapted to the cross section of the anchoring element 6 and the anchoring tool 13. The guide tool 14 can be easier manufactured if it comprises an inner part 14.1 with the bore for the guide wire 60 and with a groove adapted to the anchoring element 6, and an outer part 14.2 consisting of a thin tube in which the inner part 14.1 is fixed and which closes the groove of the inner part to constitute a channel for the anchoring element 6 and the distal end of the anchoring tool 13, and which reaches on the anchoring side (left hand side in FIG. 38A) into the bone opening and to an axial position just proximal of the groove 70 and therewith prevents too proximal exit of the liquefied material of the anchoring element.

Fixation using the set according FIGS. 38A and 38B is carried out in a similar manner as described for the set according to FIG. 37, wherein the guide wire 60 need not be removed before the anchoring step. FIGS. 38A and B show the set ready for the anchoring step, with the guide wire still in position.

FIGS. 39A/B/C illustrate a further set of fastener 3, anchoring element 6, anchoring tool 13 and guide tool 14, the set being shown in two lateral views (FIGS. 39A and 39B turned around the axis by 90° relative to FIG. 39A) and axially sectioned (FIG. 39C). The set is shown assembled and ready for the anchoring step (guide wire removed, not shown). The set is suitable for anchorage using a method as illustrated in FIG. 1. The fastener 3 comprises an inner cavity 4 which is adapted to the anchoring element 6, is connected to the circumferential fastener surface by passages 5 and may comprise a narrow distal mouth for the guide wire. For being mounted on the guide tool 14 the fastener comprises a stepped proximal profile 72 and a proximal inner thread.

The guide tool 14 comprises in inner part 14.1 and an outer part 14.2, wherein the two parts are rotatable and axially displaceable relative to each other. The inner part 14.1 of the guide tool 14 comprises the bore for introduction of the anchoring tool 13 and the anchoring element 6 and at its distal end an outer thread adapted to the inner thread of the anchor for a screwed connection 73 between the inner guide tool part 14.1 and the fastener 3. The outer guide tool part 14.2 comprises at its distal end a stepped profile 72' fitting into the stepped profile 72 of the fastener 3. The proximal end of the inner guide tool portion. 14.1 comprises a handle knob 74 positioned within a lantern shaped proximal end portion 75 of the outer guide tool part 14.2 where an operator can grip it with his fingers for rotating the inner part 14.1 relative to the outer part 14.2 of the guide tool 14.

For mounting the fastener 3 to the guide tool 14, the fastener 3 is pushed against the distal end of the guide tool 14, the stepped profiles of the fastener 3 and the distal end of the outer guide tool part 14.1 meshing. Then the inner guide tool part 14.1 is rotated for its distal end being screwed into the fastener 3 which is prevented from rotation by the meshing stepped profiles 72 and 72'. If a guide wire is used for introduction of the fastener 3 into the bone opening, the assembled set is then used as described for the set according to FIG. 37, wherein after removal of the guide wire, the anchoring element 6 and the anchoring tool 13 are introduced into the axial bore of the guide tool 14, wherein the anchoring tool 13 may already be coupled to an energy source (preferably vibration source). For such coupling e.g. the housing of a suitably adapted ultrasonic device is screwed or snapped onto the lantern shaped proximal end portion of the outer guide tool part 14.2, thereby snap-coupling the anchoring tool to the vibration generator. A suitable ultrasonic device is described e.g. in the patent application PCT/CH2010/000279, which is not published yet and whose disclosure is incorporated herein in its entirety by reference.

In the above description and appended figures a plurality of embodiments of method, fastener, and set according to the invention are disclosed wherein each figure shows a specific combination of features. One skilled in the art will easily be capable of transferring in a suitable manner selected ones of these specific features from one embodiment to another one without the need of inventiveness and without departing from the scope of the invention.

Experimental Results

Extra-graft fixations according to the invention have been realized and compared with similar fixations effected with the aid of interference screws according to the state of the art and effected with the aid of fasteners according to the invention but not being anchored in the opening (press-fitting only). Furthermore, these fixations were compared with the published data for the simple press-fit dowels as described in the initially referenced publications by Mayr et al. The comparisons regarded fixation strength, fixation stiffness, graft migration under low cycle fatigue conditions (1000 cycles of a frequency of 0.5 Hz) and final failure causes.

The fasteners used in the experiments were the fasteners as shown in FIGS. 10 to 13. These fasteners as well as the interference screws used for the comparison had a diameter of 7 mm and a length of 30 mm and were made of titanium, stainless steel, PEEK or HA-PLA. The anchoring elements were made of PLDLLA. The grafts were four-strand grafts made from bovine digital extensor from the forelimb by doubling over of two sized tendons, the final graft to pass easily through a bore of 7.5 mm diameter. The bone openings in which the grafts were fastened were tunnels of 8 mm diameter drilled through bovine tibial bone using a tibial cortex reamer.

Generally speaking the comparison showed that using the fixation according to the invention it is possible to achieve initial pull-out forces which are higher by up to 130%, initial failure forces which are higher by up to 100%, fixation stiffnesses which are higher by 40% at comparable graft migration under low cycle fatigue conditions and, compared with interference screw, less graft damage.

What is claimed is:

1. A set for fastening tissue or a prosthetic element inside an opening provided in a human or animal bone, the set comprising a fastener, the fastener comprising:
   a proximal face,
   a distal end,
   a fastener axis extending between the proximal face and the distal end and a circumferential surface extending around the fastener axis, and
   the fastener defining a guiding portion and further comprising at least one first portion of the circumferential surface and at least one second portion different from the first portion of the circumferential surface,
the set further comprising at least one anchoring element and an anchoring tool,
   wherein the anchoring element comprises a material having thermoplastic properties, and
   the anchoring tool comprises a distal end adapted to the anchoring element and is capable of transmitting energy to the anchoring element and advancing the anchoring element relative to the fastener,
the set further comprising a guide tool,
   the guide tool comprising a distal end adapted in cross section to a proximal cross section of the fastener and further comprising a through channel adapted in cross section to a distal portion of the anchoring tool,
wherein the distal end of the guide tool is adapted to hold the fastener,
   wherein the first portion comprises at least one first sector and is equipped for anchoring the fastener inside an opening,
   wherein said guiding portion comprises a material having thermoplastic properties or is equipped to guide a material having thermoplastic properties to the at least one first portion,
   wherein the second portion comprises at least one second sector designed as a pressing sector, said pressing sector being capable of clamping a tissue or prosthetic element against an inside wall of the opening, whereby the fastener is equipped for fastening the tissue or prosthetic element to the inside wall of the opening,
   wherein the at least one second sector is at least one of: flat, or substantially smooth, or comprises one of: a retainer or an axial shallow groove for accommodating the tissue or prosthetic element or a strand thereof,
   wherein the proximal face of the fastener comprises a stepped profile, and
   wherein the distal end of the guide tool comprises a stepped profile, the guide tool stepped profile meshing with the fastener stepped profile in such a manner as to prevent the fastener from rotating, and
   wherein said fastener stepped profile defines a unique radial orientation position of the fastener.

2. The set according to claim 1, wherein the first and second portions of the fastener circumferential surface are arranged as the at least one first sector and the at least one second sector alternating around the fastener axis.

3. The set according to claim 2, wherein the guiding portion comprises at least one passage connecting an inner fastener cavity, which is open at the proximal fastener face, with the at least one first sector of the circumferential surface, comprises at least one channel extending at an angle to the fastener axis from the proximal fastener face to the at least one first sector of the circumferential surface, or comprises at least one groove extending from the proximal fastener face towards the distal end of the fastener.

4. The set according to claim 3, wherein the inner cavity is distally closed, or comprises a narrower distal portion and distal mouth adapted to a guide wire.

5. The set according to claim 3, wherein the at least one anchoring element is positioned in the inner cavity, in the at least one channel, or is integrated in the fastener in a central region.

6. The set according to claim 2, wherein, for an extra-graft fixation, said at least one first sector and said at least one second sector are one first sector and one second sector, or for an intra-graft fixation said at least one second sector is a plurality of second sectors.

7. The set according to claim 1, wherein the at least one anchoring element is adapted to axially extending grooves in the circumferential surface of the fastener, to channels extending at an angle to the fastener axis from the proximal fastener face to the circumferential fastener surface, or to an inner cavity of the fastener or is integrated in a central or peripheral fastener region.

8. The set according to claim 1, wherein the anchoring element is formed as a pin or a tube.

9. The set according to claim 1, wherein the anchoring tool comprises an ultrasonic device comprising a sonotrode.

10. The set according to claim 1, wherein the guiding portion comprises at least one passage connecting an inner fastener cavity, which is open at the proximal fastener face, with the at least one first sector of the fastener circumferential surface.

11. The set according to claim 1, wherein the guiding portion includes an axially extending groove that is adapted to receive material having thermoplastic properties.

12. The set according to claim 1, wherein the guiding portion is at an angle to the fastener axis and extends from the proximal face to the at least one first sector of the fastener circumferential surface.

* * * * *